United States Patent
Ren et al.

(10) Patent No.: US 12,404,276 B2
(45) Date of Patent: Sep. 2, 2025

(54) SUBSTITUTED PYRROLO[3,4-C]PYRAZOLES FOR TREATING GASTRIC ACID-RELATED DISEASES

(71) Applicants: SHANGHAI MEDICILON INC., Shanghai (CN); MEDICILON PRECLINICAL RESEARCH (SHANGHAI) LLC., Shanghai (CN)

(72) Inventors: Feng Ren, Shanghai (CN); Xianlian Wang, Shanghai (CN); Yongmei Xu, Shanghai (CN); Chunlin Chen, Shanghai (CN); Jinna Cai, Shanghai (CN)

(73) Assignees: SHANGHAI MEDICILON INC., Shanghai (CN); MEDICILON PRECLINICAL RESEARCH (SHANGHAI) LLC., Shanghai (CN)

( * ) Notice: Subject to any disclaimer, the term of this patent is extended or adjusted under 35 U.S.C. 154(b) by 893 days.

(21) Appl. No.: 17/630,122

(22) PCT Filed: Aug. 26, 2019

(86) PCT No.: PCT/CN2019/102522
§ 371 (c)(1),
(2) Date: Jan. 25, 2022

(87) PCT Pub. No.: WO2021/017065
PCT Pub. Date: Feb. 4, 2021

(65) Prior Publication Data
US 2022/0259214 A1   Aug. 18, 2022

(30) Foreign Application Priority Data
Jul. 26, 2019  (CN) .......................... 201910679800.3

(51) Int. Cl.
*A61K 31/4162* (2006.01)
*C07D 487/04* (2006.01)

(52) U.S. Cl.
CPC ................................. *C07D 487/04* (2013.01)

(58) Field of Classification Search
CPC .......................... A61K 31/4162; C07D 487/04
USPC ........................................ 514/406; 548/360.5
See application file for complete search history.

*Primary Examiner* — Douglas M Willis
(74) *Attorney, Agent, or Firm* — Alleman Hall & Tuttle LLP

(57) ABSTRACT

A class of substituted pyrrolo[3,4-c]pyrazoles for treating gastric acid-related diseases is described as represented by the following formula (I):

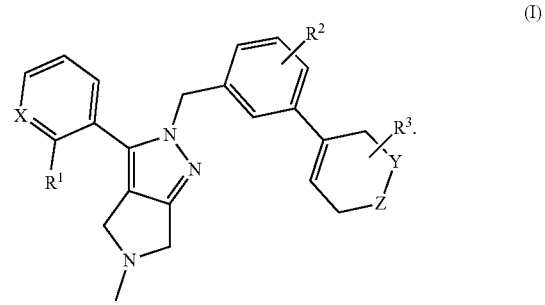

4 Claims, No Drawings

SUBSTITUTED PYRROLO[3,4-C]PYRAZOLES FOR TREATING GASTRIC ACID-RELATED DISEASES

TECHNICAL FIELD

The invention relates to a novel class of pyrrolopyrazole derivatives, to a process for their preparation, and to their use as therapeutic agents, especially as inhibitors of gastric acid secretion and as competitive acid blockers (P-CABs) of potassium ion, or pharmaceutical compositions containing them.

BACKGROUND

Peptic ulcer mainly refers to chronic ulcer that occurs in stomach and duodenum. Although there are regional differences, the incidence of peptic ulcer usually accounts for 10% to 20% of the total population, and is a frequently-occurring disease or a common disease. Ulcer formation is due to various factors, and the digestion of the mucosa by acidic gastric juice is the essential factor in ulcer formation. Therefore, inhibition of gastric acid secretion is becoming the first method for the treatment of peptic ulcer diseases.

Since the first Proton Pump Inhibitors (PPIs) omeprazole was marketed in 1988, several products of PPIs have been marketed globally to date, including lansoprazole, pantoprazole, rabeprazole, and esomeprazole. PPIs have become the first choice drugs for the treatment of gastric acid related diseases, including peptic ulcer, reflux esophagitis and Zollinger-Ellison Syndrome. The Proton Pump is essentially $H^+/K^+$-adenosine triphosphatase ($H^+/K^+$-ATPase), which specifically pumps protons ($H^+$) into the stomach cavity to form a strong acid in the stomach. Proton Pump inhibitors can inhibit the activity of the Proton Pump and thereby regulate the secretion of gastric acid mediated by the Proton Pump.

Potassium-Competitive Acid Blockers (P-CABs) are a novel class of gastric acid blockers that play a role in inhibiting the enzyme activity of H+/K+-ATPase by reversibly binding $H^+/K^+$-ATPase competitively with potassium ions ($K^+$). Compared with PPIs, the P-CABs have the characteristics of lipophilicity, alkalescence, stability under acidic (low pH) conditions and the like. At the same time, the P-CABs have the advantages of quick response, easier achievement of acid inhibition effect and the like.

The first new P-CABs drug Voronolazan was marketed in Japan in 2014 for the treatment of gastric acid-related diseases such as peptic ulcer. A series of the structures of potassium ion-competitive acid blocker have also been disclosed. However, there is still a need to develop new compounds with diversified structural types and better medicinal properties.

SUMMARY

In view of the above-mentioned problems, the object of the present invention is to provide a compound for treating gastric acid-related diseases such as peptic ulcer, which is of a novel structural type and has excellent effects and actions.

In a first aspect, the present invention provides a compound represented by general

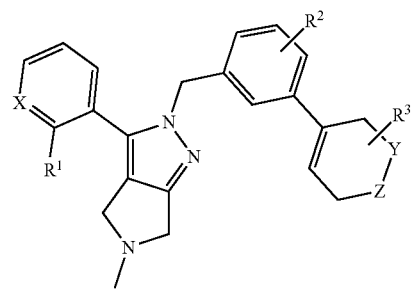

formula (I) or a pharmaceutically acceptable salt thereof, wherein:
X is selected from N or $CR^a$, wherein $R^a$ is selected from hydrogen atom or alkyl;
Y and Z are each independently selected from O, $NR^b$ or $CH_2$, and Y and Z are not both $CH_2$,
wherein $R^b$ is selected from hydrogen atom or alkyl;
$R^1$ is selected from hydrogen atom, halogen or alkyl;
$R^2$ is selected from hydrogen atom, halogen, hydroxyl or alkyl; $R^3$ is selected from hydrogen atom or alkyl.

Preferably, X is selected from N or CH; Y and Z are each independently selected from O, NH or $CH_2$, and Y and Z are not both $CH_2$; $R^1$ is selected from halogen; $R^2$ is selected from hydrogen atom, halogen or hydroxyl; $R^3$ is selected from hydrogen atom or $C_{1-3}$ alkyl group.

Preferably, X is selected from N or CH; Y is O and Z is $CH_2$; or Y is $CH_2$ and Z is O or NH; $R^1$ is fluorine atom; $R^2$ is derived from hydrogen atom, fluorine atom, chlorine atom or hydroxyl; $R^3$ is hydrogen atom.

Preferably, the compound is selected from:
2-(3,6-dihydro-2H-pyran-4-yl)-4-((3-(2-fluorophenyl)-5-methyl-5,6-dihydropyrrolo[3,4-c]pyrazole-2(4H)-yl)methyl)phenol;
2-(5,6-dihydro-2H-pyran-3-yl)-4-((3-(2-fluorophenyl)-5-methyl-5,6-dihydropyrrolo[3,4-c]pyrazole-2(4H)-yl)methyl)phenol;
2-(3-(5,6-dihydro-2H-pyran-3-yl)benzyl)-3-(2-fluorophenyl)-5-methyl-2,4,5,6-tetrahydropyrrolo[3,4-c]pyrazole;
(5,6-dihydro-2H-pyran-3-yl)-5-((3-(2-fluorophenyl)-5-methyl-5,6-dihydropyrrolo[3,4-c]pyrazole-2(4H)-yl)methyl)phenol;
2-(3-(3,6-dihydro-2H-pyran-4-yl)benzyl)-3-(2-fluorophenyl)-5-methyl-2,4,5,6-tetrahy dropyrrolo[3,4-c]pyrazole;
(3-chloro-5-(3,6-dihydro-2H-pyran-4-yl)benzyl)-3-(2-fluorophenyl)-5-methyl-2,4,5,6-tetrahydropyrrolo[3,4-c]pyrazole;
2-(3-(3,6-dihydro-2H-pyran)-4-yl)-4-fluorobenzyl)-3-(2-fluorophenyl)-5-methyl-2,4,5,6-tetrahydropyrrolo[3,4-c]pyrazole;
3-(3,6-dihydro-2H-pyran-4-yl)-5-((3-(2-fluorophenyl)-5-methyl-5,6-dihydropyrrolo[3,4-c]pyrazole-2(4H)-yl)methyl)phenol;
3-(2-fluorophenyl)-5-methyl-2-(3-(1,2,3,6-tetrahydro(Pyridin-4-yl)benzyl)-2,4,5,6-tetrahydropyrrolo[3,4-c]pyrazole;
2-(3-(3,6-dihydro-2H-pyran-4-yl)benzyl)-3-(2-fluoropyridin-3-yl)-5-methyl-2,4,5,6-tetrahydropyrrolo[3,4-c]pyrazole.

In a second aspect, the present invention provides a pharmaceutical composition, comprising the compound represented by general formula (I) or a pharmaceutically acceptable salt thereof, and a pharmaceutically acceptable carrier, excipient, or diluent.

In a third aspect, the present invention provides an application of the compound represented by general formula (I) or the pharmaceutically acceptable salt thereof, and the above-mentioned pharmaceutical composition in preparing a gastric acid secretion inhibitor.

In a fourth aspect, the present invention provides an application of the compound represented by general formula (I) or the pharmaceutically acceptable salt thereof, and the above-mentioned pharmaceutical composition in preparing an $H^+/K^+$-adenosine triphosphatase inhibitor.

In a fifth aspect, the present invention provides an application of the compound represented by general formula (I) or the pharmaceutically acceptable salt thereof, and the above-mentioned pharmaceutical composition in preparing a potassium ion competitive acid blocker.

In a sixth aspect, the present invention provides an application of the compound represented by general formula (I) or the pharmaceutically acceptable salt thereof, and the above-mentioned pharmaceutical composition in preparing a medicament for the treatment and/or prevention of peptic ulcer, Zollinger-Ellison Syndrome, gastritis, erosive esophagitis, reflux esophagitis, symptomatic gastroesophageal reflux disease, Barrett's esophagitis, functional dyspepsia, *Helicobacter pylori* infection, gastric cancer, gastric MALT lymphoma, ulcers caused by non-steroidal anti-inflammatory drugs, or hyperacidity or ulcers caused by post-operative stress; or inhibiting peptic ulcer, acute stress ulcer, hemorrhagic gastritis, or upper gastrointestinal bleeding caused by invasive stress.

DETAILED DESCRIPTION

The present invention will be further described below through the following embodiments. It should be understood that the following embodiments are only used to illustrate the present invention, not to limit the present invention.

Unless stated to the contrary, the following terms used in the specification and claims have the following meanings.

The term "alkyl" refers to a saturated aliphatic hydrocarbon group, including straight or branched chain groups of 1 to 10 carbon atoms. Preferably, an alkyl groups containing 1 to 5 carbon atoms. More preferably, an alkyl group containing 1 to 3 carbon atoms, such as methyl, ethyl, n-propyl, isopropyl.

The carbon atom content of various hydrocarbon-containing moieties is indicated by the prefix designating the minimum and maximum number of carbon atoms for that moiety, i.e., the prefixes $C_{i-j}$ indicate that the number of carbon atoms for that moiety ranges from integers "i" to integers "j" (including i and j). Thus, for example, $C_{1-3}$ alkyl refers to alkyl groups of 1 to 3 carbon atoms (including 1 and 3).

The term "hydroxy" refers to an —OH group.

The term "halogen" refers to fluorine, chlorine, bromine or iodine.

Unless otherwise specified, all occurrences of the compounds herein are intended to comprise all possible isomers, such as tautomers, enantiomers, diastereomers, and mixtures thereof.

The term "compound of the present invention" refers to a compound represented by the general formula (I). The term also comprises various crystalline forms of the compound of general formula (I), pharmaceutically acceptable salts, hydrates or solvates.

The term "pharmaceutically acceptable salt" refers to salts formed by the compounds of the present invention with acids or bases that are suitable for use as pharmaceutical agents. Pharmaceutically acceptable salts include inorganic salts and organic salts. One preferred class of salts is that formed from the compounds of the present invention and acids. Suitable acids for forming salt include, but are not limited to: inorganic acids such as hydrochloric acid, hydrobromic acid, hydrofluoric acid, sulfuric acid, nitric acid, phosphoric acid, etc., organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, phenylmethanesulfonic acid, benzenesulfonic acid, etc.; and acidic amino acids such as aspartic acid and glutamic acid.

The term "pharmaceutically acceptable carrier" refers to a carrier that can be used in the preparation of pharmaceutical compositions, which are generally safe, non-toxic, not biologically or otherwise undesirable, and comprises carriers that are pharmaceutically acceptable by animals and humans. As used in the specification and claims, a "pharmaceutically acceptable carrier" comprises one or more such carriers.

The terms "comprise", "contain" or "include" mean that the various ingredients may be used together in a mixture or composition of the present invention. Therefore, the terms "mainly consist of" and "consist of" are encompassed by the term "comprise".

The term "prevention" refers, for example, to the prevention of development of clinical symptoms of a disease in a mammal that may be exposed to or predisposed to the disease but has not yet experienced or displayed symptoms of the disease.

The term "treatment" may refer to inhibiting a disease, such as preventing or reducing the development of a disease or clinical symptoms thereof, or relieving a disease, such as causing regression of a disease or clinical symptoms thereof.

Compound of General Formula (I)

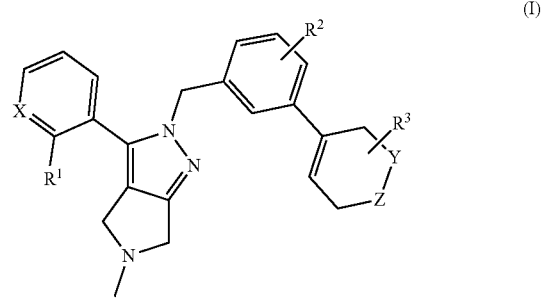

wherein:

X is selected from N or $CR^a$, wherein $R^a$ is selected from hydrogen atom or alkyl;

Y and Z are each independently selected from O, $NR^b$ or $CH_2$, and Y and Z are not both $CH_2$, wherein $R^b$ is selected from hydrogen atom or alkyl;

$R^1$ is selected from hydrogen atom, halogen or alkyl;

$R^2$ is selected from hydrogen atom, halogen, hydroxyl or alkyl; $R^3$ is selected from hydrogen atom or alkyl.

In some embodiments of the present invention, X is selected from N or CH.

In some embodiments of the present invention, Y and Z are selected from O, NH or $CH_2$, and Y and Z are not both $CH_2$. In a more preferred embodiment, Y is O, while Z is $CH_2$; or Y is $CH_2$ and Z is O or NH.

In some embodiments of the present invention, $R^1$ is selected from halogen. In a more preferred embodiment, $R^1$ is fluorine atom.

In some embodiments of the present invention, R² is selected from hydrogen atom, halogen or hydroxyl. In a more preferred embodiment, R² is selected from hydrogen atom, fluorine atom, chlorine atom, or hydroxyl.

In some embodiments of the present invention, R² is ortho or meta to the ring containing R³.

In some embodiments of the present invention, R³ is selected from hydrogen atom or $C_{1-3}$ alkyl group. In a more preferred embodiment, $R_3$ is hydrogen atom.

In some embodiments of the present invention, the compound of general formula (I) is selected from the compounds shown in Table 1.

TABLE 1

| Compound number | Compound structure | Compound naming |
| --- | --- | --- |
| 1 | 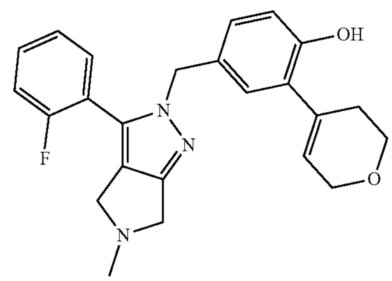 [SMILES: CN1Cc2nn(Cc3ccc(O)c(C4=CCOCC4)c3)c(-c3ccccc3F)c2C1] | 2-(3,6-dihydro-2H-pyran-4-yl)-4-((3-(2-fluorophenyl)-5-methyl-5,6-dihydropyrrolo[3,4-c]pyrazole-2(4H)-yl)methyl)phenol; |
| 2 | 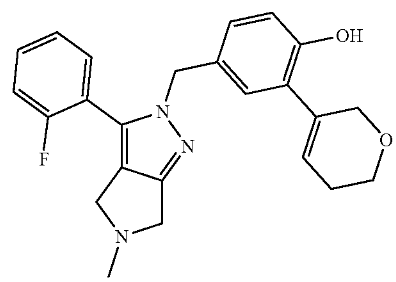 [SMILES: CN1Cc2nn(Cc3ccc(O)c(C4=CCCOC4)c3)c(-c3ccccc3F)c2C1] | 2-(5,6-dihydro-2H-pyran-3-yl)-4-((3-(2-fluorophenyl)-5-methyl-5,6-dihydropyrrolo[3,4-c]pyrazole-2(4H)-yl)methyl)phenol; |
| 3 | 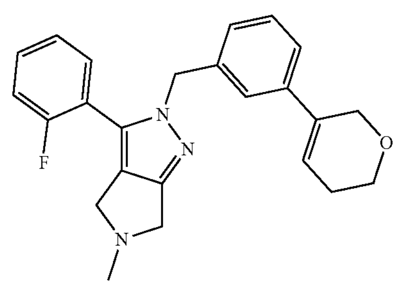 [SMILES: CN1Cc2nn(Cc3cccc(C4=CCCOC4)c3)c(-c3ccccc3F)c2C1] | 2-(3-(5,6-dihydro-2H-pyran-3-yl)benzyl)-3-(2-fluorophenyl)-5-methyl-2,4,5,6-tetrahydropyrrolo[3,4-c]pyrazole; |
| 4 | 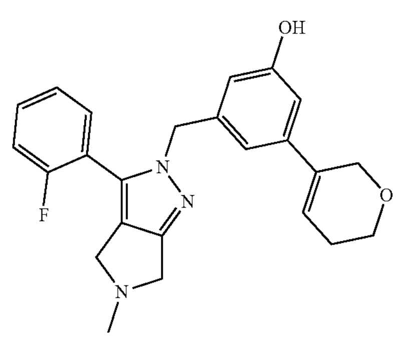 [SMILES: CN1Cc2nn(Cc3cc(O)cc(C4=CCCOC4)c3)c(-c3ccccc3F)c2C1] | 3-(5,6-dihydro-2H-pyran-3-yl)-5-((3-(2-fluorophenyl)-5-methyl-5,6-dihydropyrrolo[3,4-c]pyrazole-2(4H)-yl)methyl)phenol; |

TABLE 1-continued

| Compound number | Compound structure | Compound naming |
| --- | --- | --- |
| 5 | 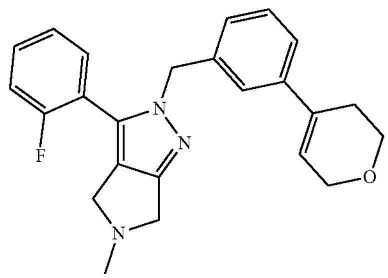 [SMILES: CN1Cc2nn(Cc3cccc(C4=CCOCC4)c3)c(-c3ccccc3F)c2C1] | 2-(3-(3,6-dihydro-2H-pyran-4-yl)benzyl)-3-(2-fluorophenyl)-5-methyl-2,4,5,6-Tetrahydropyrrolo[3,4-c]pyrazole; |
| 6 | 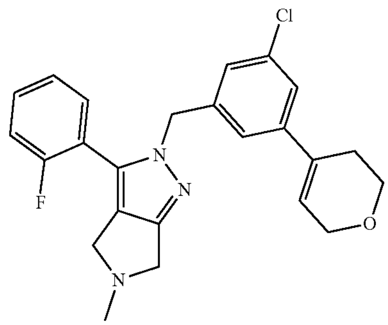 [SMILES: CN1Cc2nn(Cc3cc(Cl)cc(C4=CCOCC4)c3)c(-c3ccccc3F)c2C1] | (3-chloro-5-(3,6-dihydro-2H-pyran-4-yl)benzyl)-3-(2-fluorophenyl)-5-methyl-2,4,5,6-tetrahydropyrrolo[3,4-c]pyrazole; |
| 7 | 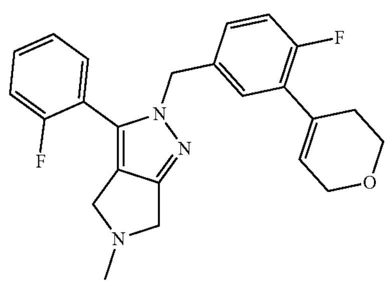 [SMILES: CN1Cc2nn(Cc3ccc(F)c(C4=CCOCC4)c3)c(-c3ccccc3F)c2C1] | 2-(3-(3,6-dihydro-2H-pyran)-4-yl)-4-fluorobenzyl)-3-(2-fluorophenyl)-5-methyl-2,4,5,6-tetrahydropyrrolo[3,4-c]pyrazole; |
| 8 | 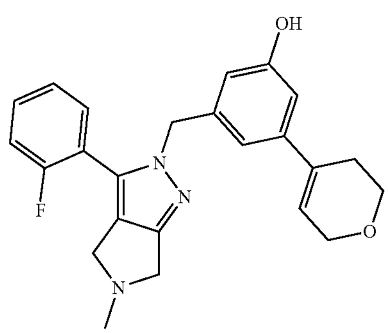 [SMILES: CN1Cc2nn(Cc3cc(O)cc(C4=CCOCC4)c3)c(-c3ccccc3F)c2C1] | 3-(3,6-dihydro-2H-pyran-4-yl)-5-((3-(2-fluorophenyl)-5-methyl-5,6-dihydropyrrolo[3,4-c]pyrazole-2(4H)-yl)methyl)phenol; |
| 9 | 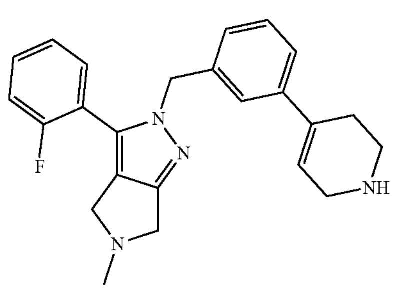 [SMILES: CN1Cc2nn(Cc3cccc(C4=CCNCC4)c3)c(-c3ccccc3F)c2C1] | 3-(2-fluorophenyl)-5-methyl-2-(3-(1,2,3,6-tetrahydro(Pyridin-4-yl)benzyl)-2,4,5,6-tetrahydropyrrolo[3,4-c]pyrazole; |

TABLE 1-continued

| Compound number | Compound structure | Compound naming |
|---|---|---|
| 10 | 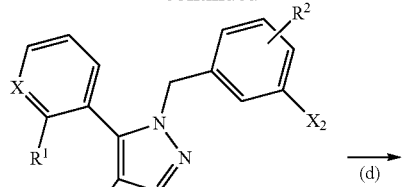 | 2-(3-(3,6-dihydro-2H-pyran-4-yl)benzyl)-3-(2-fluoropyridin-3-yl)-5-methyl-2,4,5,6-tetrahydropyrrolo[3,4-c]pyrazole. |

Preparation Method of the Compound of General Formula (I)

In some embodiments of the present invention, the compounds of general formula (I) may be prepared using the following general synthetic route:

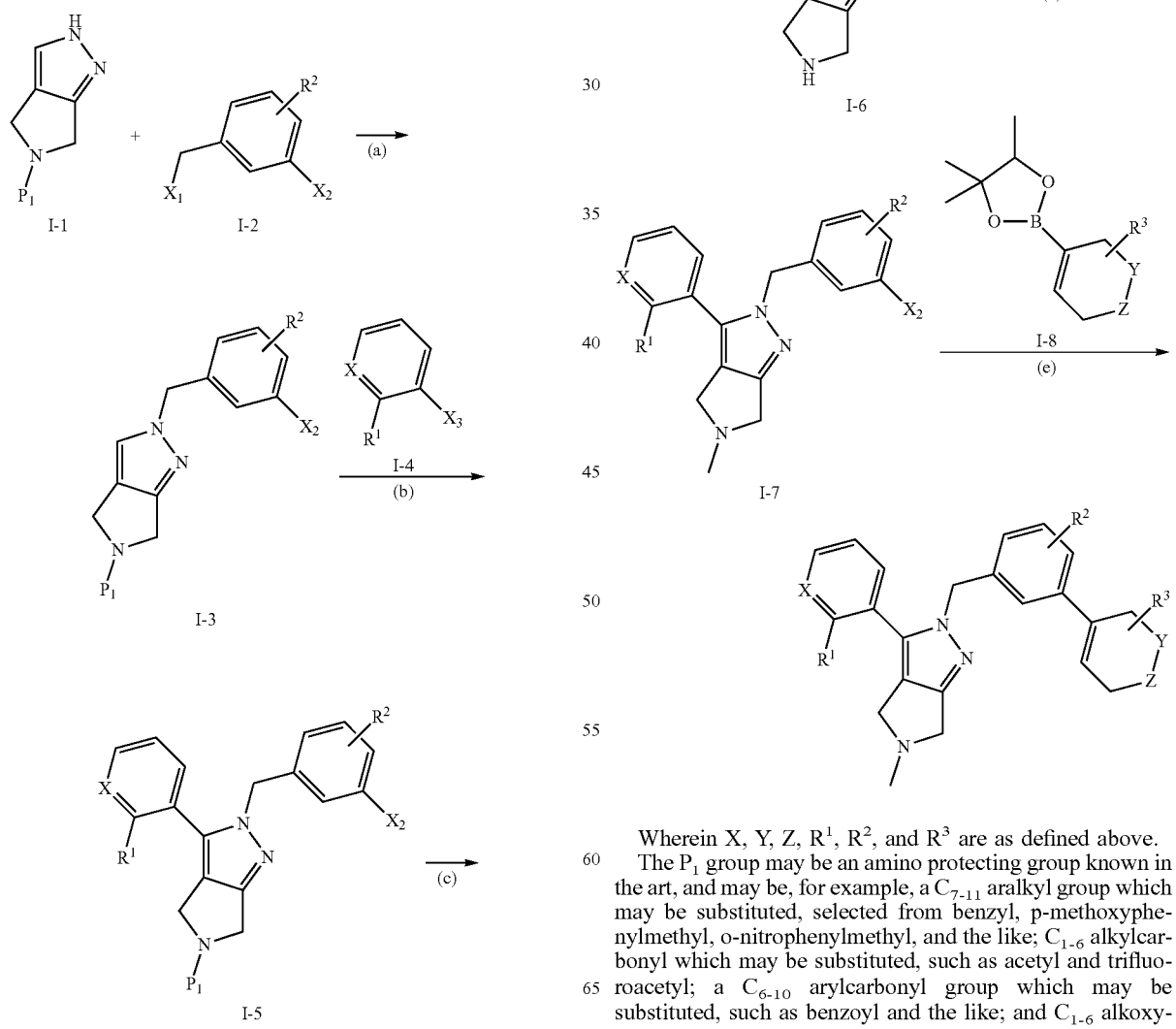

Wherein X, Y, Z, $R^1$, $R^2$, and $R^3$ are as defined above.

The $P_1$ group may be an amino protecting group known in the art, and may be, for example, a $C_{7-11}$ aralkyl group which may be substituted, selected from benzyl, p-methoxyphenylmethyl, o-nitrophenylmethyl, and the like; $C_{1-6}$ alkylcarbonyl which may be substituted, such as acetyl and trifluoroacetyl; a $C_{6-10}$ arylcarbonyl group which may be substituted, such as benzoyl and the like; and $C_{1-6}$ alkoxycarbonyl which may be substituted, such as methoxycarbonyl, ethoxycarbonyl, Boc (tert-butoxycarbonyl), Cbz (Benzyloxycarbonyl), Fmoc (fluorenylmethyloxycarbonyl), Teoc (trimethylsilylethoxycarbonyl) and the like; an alkenyloxycarbonyl group such as Alloc (allyloxycarbonyl) and the like; an alkylsulfonyl group such as methylsulfonyl and the like; $C_{6-10}$ arylsulfonyl which may be substituted, such as p-toluenesulfonyl and the like.

The $X_1$ group may be a leaving group known in the art, and may be selected from, for example, halogen atom such as fluorine atom, chlorine atom, bromine atom, iodine atom, etc.

The $X_2$ group may be selected from halogen atom such as chlorine atom, bromine atom, iodine atom, etc.

The $X_3$ group may be selected from halogen atom such as chlorine atom, bromine atom, iodine atom, etc.

In step (a), the compound of formula I-1 is reacted with the compound of formula I-2 to obtain the compound of formula I-3.

The molar ratio of the compound of formula I-1 to the compound of formula I-2 can be 1:(0.5 to 3.0). The reaction solvent may be acetonitrile, acetone, tetrahydrofuran, dioxane, N,N-dimethylformamide, etc. The reaction of step (a) may be carried out in the presence of a base. The base can be selected from: cesium carbonate, potassium carbonate, sodium carbonate, potassium hydroxide, sodium hydroxide, and the like. The molar ratio of the compound of formula I-1 to the base can be 1:(1.0 to 6.0). The reaction temperature of step (a) may be appropriately set by those skilled in the art, and may be, for example, 0 to 100° C.

In step (b), the compound of formula I-3 is reacted with the compound of formula I-4 to obtain the compound of formula I-5.

The molar ratio of the compound of formula I-3 to the compound of formula I-4 can be 1:(0.5 to 3.0). The reaction solvent may be acetonitrile, acetone, tetrahydrofuran, dioxane, N,N-dimethylformamide, etc. Step (b) may be carried out in the presence of a palladium catalyst. The palladium catalyst can be selected from: allylpalladium(II) chloride dimer, tris(dib enzylideneacetone)dipalladium, [1,1'-bis(diphenylphosphino)ferrocene] Palladium dichloride, palladium chloride, and the like. Alternatively, the reaction of step (b) may be carried out in the presence of a base. The base may be selected from: potassium acetate, sodium acetate, potassium phosphate, potassium dihydrogen phosphate, potassium bistrimethylsilyl amine, sodium bistrimethylsilyl amine, and the like. The molar ratio of the compound of formula I-3 to the base can be 1:(0.5 to 3.0). The reaction temperature in step (b) may be appropriately set by those skilled in the art, and may be, for example, 40 to 150° C.

In step (c), the $P_1$ protecting group is removed. The reaction conditions may be those commonly used in the art for deprotecting an amino-protecting group. For example, when P1 is Boc, it can be treated with a protic acid (for example, trifluoroacetic acid) or a Lewis acid.

In step (d), the compound of formula I-6 is subjected to an aminomethylation reaction to obtain the compound of formula I-7. This step may employ aminomethylation reaction conditions well known in the art. In some embodiments, the compound of formula I-6 is stirred with formaldehyde for a period of time to generate a Schiff base, and then reacted with a reducing agent, such as sodium borohydride acetate, for a period of time to obtain the compound of formula I-7.

In step (e), the compound of formula I-7 is reacted with the compound of formula I-8 to obtain the compound of general formula (I).

The molar ratio of the compound of formula I-7 to the compound of formula I-8 can be 1:(0.5 to 5.0). The reaction solvent may be dioxane, tetrahydrofuran, toluene, N,N-dimethylformamide, etc. Step (e) can be carried out in the presence of a palladium catalyst. The palladium catalyst can be selected from: [1,1'-bis(diphenylphosphino)ferrocene] palladium dichloride, allylpalladium(II) chloride dimer, tris (dibenzylidene) Acetone) dipalladium, palladium chloride, and the like. Alternatively, the reaction of step (e) may be carried out in the presence of a base. The base may be selected from: potassium carbonate, sodium carbonate, sodium bicarbonate, cesium carbonate, potassium phosphate, and the like. The molar ratio of the compound of formula I-7 to the base can be 1:(0.5 to 5.0). The reaction temperature in step (e) can be appropriately set by those skilled in the art, and may be, for example, 40 to 150° C.

Application of the Compounds of General Formula (I)

The compounds of general formula (I) can be used as inhibitors of gastric acid secretion.

The compounds of general formula (I) can be used as $H^+/K^+$-ATPase inhibitors.

The compounds of general formula (I) can be used as potassium ion competitive acid blockers (P-CABs).

The compounds of general formula (I) can be used for treating and/or preventing peptic ulcer, Zollinger-Ehrlich syndrome, gastritis, erosive esophagitis, reflux esophagitis, symptomatic gastroesophageal reflux disease, Barrett's esophagitis, functional dyspepsia, *Helicobacter pylori* infection, gastric cancer, gastric MALT lymphoma, ulcers caused by non-steroidal anti-inflammatory drugs, or hyperacidity or ulcers caused by post-operative stress; or inhibiting peptic ulcers, acute stress ulcers, Haemorrhagic gastritis or upper gastrointestinal bleeding caused by invasive stress. The aforementioned peptic ulcer includes, but is not limited to, gastric ulcer, duodenal ulcer or anastomotic ulcer. Symptomatic gastroesophageal reflux disease includes, but is not limited to, non-erosive reflux disease or gastroesophageal reflux disease without esophagitis.

Pharmaceutical Composition

The pharmaceutical composition of the present invention comprises an effective amount of the compound represented by the general formula (I) or tautomer, enantiomer, diastereomer, mixture form thereof, pharmaceutically acceptable salt thereof, and pharmaceutically acceptable carrier or excipient or diluent.

"Effective amount" means the compound of the present invention: (i) treating a particular disease, condition or disorder, (ii) attenuating, ameliorating or eliminating one or more symptoms of a particular disease, condition or disorder, or (iii) preventing or delaying the onset of one or more symptoms of a particular disease, condition, or disorder described herein.

Examples of pharmaceutically acceptable carriers moieties are cellulose and its derivatives (e.g., sodium carboxymethyl cellulose, sodium ethyl cellulose, cellulose acetate, etc.), gelatin, talc, and solid lubricants (e.g., stearic acid, magnesium stearate), calcium sulfate, vegetable oils (e.g., soybean oil, sesame oil, peanut oil, olive oil, etc.), polyols (e.g., propylene glycol, glycerin, mannitol, sorbitol, etc.), emulsifiers (e.g., Tween), wetting agents (e.g., sodium lauryl sulfate), colorants, flavors, stabilizers, antioxidants, preservatives, pyrogen-free water, and the like.

The mode of administration of the compounds or pharmaceutical compositions of the present invention is not particularly limited, and representative modes of administration include (but are not limited to): oral, intratumoral, rectal, parenteral (intravenous, intramuscular, or subcutaneous), and topical administration.

The compounds of the present invention may be administered alone or in combination with other pharmaceutically acceptable compounds.

Another aspect of the present invention relates to a method of inhibiting the secretion of gastric acid, which comprises administering to a patient in need of an effective amount of the compound represented by the general formula (I) or its tautomers, enantiomers, and diastereomers, and mixtures thereof, and pharmaceutically acceptable salts or pharmaceutical compositions thereof.

Another aspect of the present invention relates to a method for inhibiting $H^+/K^+$-adenosine triphosphatase ($H^+/K^+$-ATPase) comprising administering to a patient in need of an effective amount of the compound of formula (I) or its tautomers, enantiomers, diastereomers, and mixtures thereof, and pharmaceutically acceptable salts thereof or pharmaceutical compositions thereof.

Hereinafter, the present invention will be further described with the specific examples. It should be understood that the following examples are used to explain this invention and do not mean to limit the scope of this invention. The experimental methods that do not indicate specific conditions in the following examples usually follow the conventional conditions or the conditions recommended by the manufacturer. Unless otherwise stated, percentages and parts are calculated by weight.

The structure of the compound is determined by nuclear magnetic resonance (NMR) or mass spectrometry (MS), and the purity of the compound is determined by liquid high pressure chromatography (HPLC). NMR was measured using a Bruker AVANCE-400 nuclear magnetic resonance apparatus in deuterated dimethyl sulfoxide (DMSO-d6) or deuterated methanol (MeOH-d4) as the solvent and tetramethylsilane (TMS) as the internal standard and chemical shifts in ppm. MS was determined using an Agilent 6120 mass spectrometer. HPLC was measured using an Agilent 1200DAD high pressure liquid chromatograph.

Example 1

2-(3,6-dihydrohydro-2H-pyran-4-yl)-4-(3-(2-fluoro-knowledge)-5-methylmethylpyrrolo[3,4-c]pyrazole-2(4H)-yl)methyl)phenol

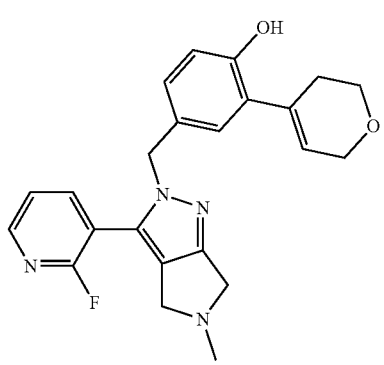

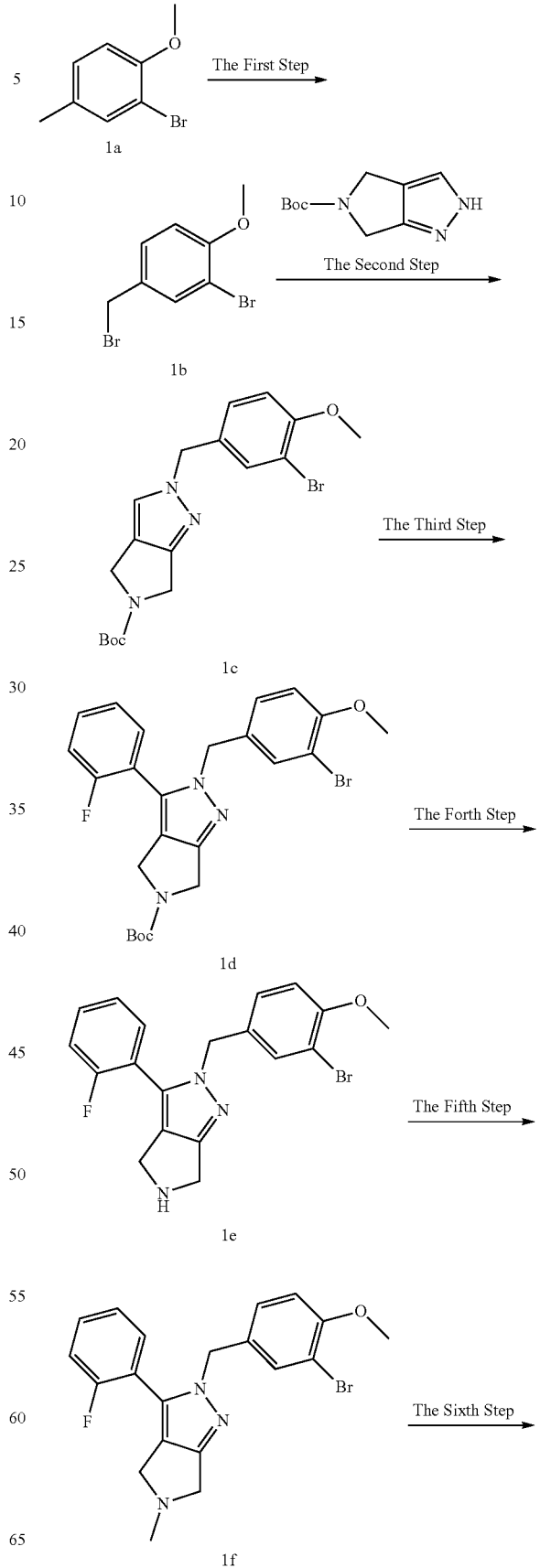

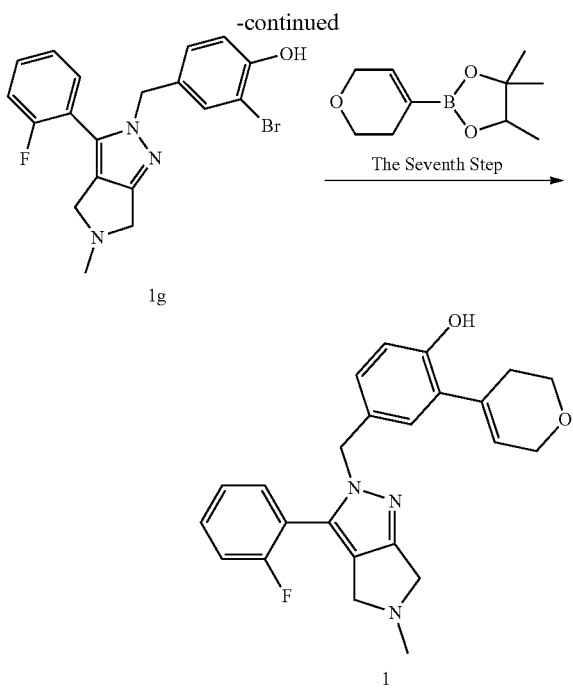

The First Step:
2-bromo-4-(bromomethyl)-1-methoxybenzene 2-bromo-1-methoxy-4-methylbenzene 1a (5 g, 24.8 mmol) was added into a round bottom flask, dissolved in 30 mL of dichloromethane, and N-bromosuccinimide (5.3 g, 29.8 mmol) and azobisisobutyronitrile (6.8 g, 42 mmol) were added thereto, and the mixture was heated at 40° C. and refluxed overnight. After the reaction, the reaction was returned to room temperature, and water (20 mL) was added, washed with ethyl acetate (40 mL×3) and brine (40 mL×2), then dried with anhydrous sodium sulfate, filtered and concentrated to obtain 2-bromo-4-(bromomethyl)-1-methoxybenzene 1b (5.6 g, yellow solid), yield: 81.5%. 1H NMR (400 MHz, CDCl$_3$) δ 7.59 (d, J=2.0 Hz, 1H), 7.32-7.26 (m, 1H), 6.86 (d, J=8.4 Hz, 1H), 4.44 (s, 2H), 3.89 (s, 3H). MS m/z (ESI): 278.8 [M+H].

The Second Step

2-(3-bromo-4-methoxybenzyl)-2,6-dihydropyrrolo[3,4-c]pyrazole-5(4H)-carboxylic acid tert-butyl ester 2,6-dihydropyrrolo[3,4-c]pyrazole-5(4H)-carboxylic acid tert-butyl ester (2.8 g, 13.5 mmol) was dissolved in acetonitrile (50 mL), and 2-bromo-4-(Bromomethyl)-1-methoxybenzene 1b (4.5 g, 16.2 mmol) and cesium carbonate (32.5 g, 47 mmol) were added, purged for 3 times with nitrogen, and placed in an 80° C. oil bath for reaction for 3 hours. The reaction solution was filtered, and the filtrate was concentrated. The residue was purified by column chromatography separation (the ratio of petroleum ether and ethyl acetate was equal to 2:1) to obtain 2-(3-bromo-4-methoxybenzyl)-2,6-dihydropyrrolo[3, 4-c]pyrazole-5(4H)-carboxylic acid tert-butyl ester 1c (6 g, yellow oil), yield: 91%. MS m/z (ESI): 408.0 [M+H].

The Third Step

2-(3-bromo-4-methoxybenzyl)-3-(2-fluorophenyl)-2,6-dihydropyrrolo[3,4-c]pyrazole-5(4H)-tert-butyl carboxylate 2-(3-bromo-4-methoxybenzyl)-2,6-dihydropyrrolo[3,4-c]pyrazole-5(4H)-carboxylic acid tert-butyl carboxylate 1c (4.6 g, 13.7 mmol), potassium acetate (8 g, 82.2 mmol), allylpalladium(II) chloride dimer (499 mg, 1.37 mmol), N,N-dimethylacetamide (50 mL) and o-fluoroiodobenzene (6.1 g, 27.4 mmol) were added into a round bottom flask one by one. After the oil pump was purged for four times (argon), the mixture was placed into an oil bath that was heated to 100° C. in advance for reaction for 3 hours. After the reaction was returned to room temperature, the reaction solution was poured directly into water (80 mL), and extracted with ethyl acetate (40 mL×3). The organic phase was washed with brine (40 mL×2), then dried over anhydrous sodium sulfate, filtered and concentrated. The crude product was separated by column chromatography (the ratio of petroleum ether and ethyl acetate was equal to 3/1) to obtain 2-(3-bromo-4-methoxybenzyl)-3-(2-fluorophenyl)-2, 6-dihydropyrrolo[3,4-c]pyrazole-5(4H)-carboxy tert-butyl acid 1d (729 mg, yellow oil), yield: 10.6%. MS m/z (ESI): 502.1 [M+H].

The Fourth Step

2-(3-bromo-4-methoxybenzyl)-3-(2-fluorophenyl)-2,4,5,6-tetrahydropyrrolo[3,4-c]pyrazole Trifluoroacetic acid (0.5 mL) was added into a solution of 2-(3-Bromo-4-methoxybenzyl)-3-(2-fluorophenyl)-2,6-dihydropyrrolo[3,4-c]pyrazole-5(4H)-carboxy Tert-butyl ester 1d (729 mg, 1.45 mmol) in dichloromethane (1.5 mL) at room temperature for reaction for 1 hour. After the reaction, the mixture was directly concentrated to obtain the crude product 2-(3-bromo-4-methoxybenzyl)-3-(2-fluorophenyl)-2,4,5,6-tetrahydropyrrolo[3,4-c]pyrazole 1e (581 mg, brown oil), yield: 100%. MS m/z (ESI): 403.2 [M+H].

The Fifth Step

2-(3-bromo-4-methoxybenzyl)-3-(2-fluorophenyl)-5-methyl-2,4,5,6-tetrahydropyrrolo[3,4-c]pyrazole Aqueous formaldehyde solution (37%, 1.2 g, 14.5 mmol) was added into 2-(3-bromo-4-methoxybenzyl)-3-(2-fluorophenyl)-2,4,5,6-tetrahydropyrrolo[3,4-c]pyrazole 1e (581 mg, 1.45 mmol) in dichloromethane/methanol (6 mL, 2/1) solution and stirred at room temperature for half an hour. Sodium acetate borohydride (1.8 g, 8.7 mmol) was slowly added into the reaction solution for reaction at room temperature overnight. After the reaction solution was concentrated, the mixture was dissolved and diluted with dichloromethane (10 mL), and then washed with ammonia/water (10 mL×2, ⅕) and saturated brine (10 mL) in sequence. The organic phase was dried with anhydrous sodium sulfate and concentrated. 50 mg of crude product was taken and prepared by high pressure liquid chromatography (acetonitrile/water (containing 0.05% trifluoroacetic acid)) to obtain 2-(3-bromo-4-methoxybenzyl)-3-(2-fluorophenyl)-5-Methyl-2,4,5,6-tetrahydropyrrolo[3,4-c]pyrazole if (trifluoroacetate, salt coefficient=1.3, 20.1 mg, yellow oil), yield: 24.5%. MS m/z (ESI): 416.0 [M+H]. $^1$H NMR (400 MHz, CDCl3) δ 7.50-7.46 (m, 1H), 7.25-7.07 (m, 4H), 6.97 (d, J=8.4 Hz, 1H), 6.80 (d, J=8.4 Hz, 1H), 5.17 (s, 2H), 4.96 (s, 1H), 4.09-4.01 (m, 2H), 3.86 (s, 3H), 3.18 (s, 3H).

The Sixth Step 2-bromo-4-((3-(2-fluorophenyl)-5-methyl-5,6-dihydropyrrolo[3,4-c]pyrazole-2(4H)-yl)methyl)phenol 2-(3-bromo-4-methoxybenzyl)-3-(2-fluorophenyl)-5-methyl-2,4,5,6-tetrahydropyrrolo[3,4-c]pyrazole 1f (50 mg, 0.11 mmol) was weighed and added into a round bottom flask, dichloromethane (1 mL) was added, and boron tribromide (0.1 mL) was then added under ice bath for reaction for 2 hours. After the reaction was completed, the mixture was quenched with water (5 mL) and extracted with dichloromethane (5 mL×3). The organic phase was washed with brine (5 mL×2), then dried over anhydrous sodium sulfate, filtered and concentrated. The crude product obtained was prepared by high pressure liquid chromatography (acetonitrile/water (containing 0.05% trifluoroacetic acid)) to obtain 2-bromo-4-((3-(2-fluorophenyl)-5-methyl-5,6-dihydropyrrolo[3,4-c]pyrazole-2(4H)-yl)methyl)phenol 1g (trifluoro Acetate, salt coefficient=1.6, 29.9 mg, light yellow oil), yield: 46.5%. MS m/z (ESI): 402.2 [M+H]. ¹H NMR (400 MHz, CDCl₃) δ 7.52-7.47 (m, 1H), 7.27-7.10 (m, 4H), 6.87 (q, J=8.4 Hz, 2H), 6.70 (s, 1H), 5.15 (s, 2H), 4.94 (d, J=12.8 Hz, 2H), 4.12-4.02 (m, 2H), 3.13 (s, 3H).

The Seventh Step 2-(3,6-dihydro-2H-pyran-4-yl)-4-((3-(2-fluorophenyl)-5-methyl-5,6-dihydropyrrolo[3,4-c]pyrazole-2(4H)-yl)methyl)phenol 2-bromo-4-((3-(2-fluorophenyl)-5-methyl-5,6-dihydropyrrolo[3,4-c]pyrazole-2(4H)-Yl)methyl)phenol 1g (80 mg, 0.21 mmol), 2-(3,6-dihydro-2H-pyran-4-yl)-4,4,5trimethyl-1,3,2-Dioxaborane (53 mg, 0.25 mmol), [1,1'-bis(diphenylphosphino) ferrocene] palladium dichloride (15 mg, 0.02 mmol), potassium carbonate (58 mg, 0.42 mmol), Dioxane (0.8 mL) and water (0.2 mL) were added one by one in a microwave tube. After purging (argon) for three times, the oil bath was heated to 80° C., and the temperature was kept and stirred for 1.5 hours. After the reaction, the mixture was cooled to room temperature, and filtered, the filtrate was extracted with ethyl acetate (30 mL*3). The organic phase was washed with brine (10 mL*2), then dried over anhydrous sodium sulfate, filtered and concentrated. The crude product was separated by combi-flash (normal phase silica gel column, 25 g, dichloromethane: dichloromethane/methanol mixed solvent (volume ratio v/v=10/1)=0-50%) to obtain the crude product, and then prepared by HPLC (Acetonitrile/water (containing 0.05% trifluoroacetic acid) gradient washing), purification to obtain the target compound 2-(3,6-dihydro-2H-pyran-4-yl)-4-((3-(2-fluorobenzene) Yl)-5-methyl-5,6-dihydropyrrolo[3,4-c]pyrazole-2 (4H)-yl)methyl)phenol 1 (trifluoroacetate, salt coefficient=3.06, Salt-containing molecular weight: 739.35, 9.76 mg, colorless solid), yield: 11.9%. MS m/z (ESI): 406.4 [M+H]. 1H NMR (400 MHz, MeOD) δ7.52-7.49 (m, 1H), 7.38-7.22 (m, 3H), 6.73-6.56 (m, 3H), 5.75 (s, 1H), 5.17 (s, 2H), 4.30 (d, J=1.6 Hz, 2H), 4.08 (s, 2H), 3.97 (s, 2H), 3.80 (t, J=5.6 Hz, 2H), 2.79 (s, 3H), 2.28-2.21 (m, 2H).

Example 2

2-(5,6-dihydro-2H-pyran-3-yl)-4-((3-(2-fluorophenyl)-5-methyl-5,6-dihydropyrrolo[3,4-c]pyrazole-2 (4H)-yl)methyl)phenol

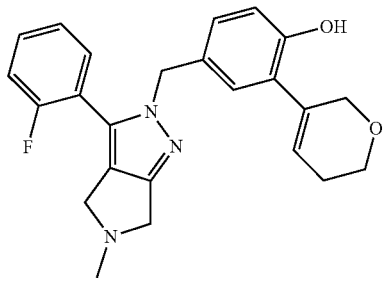

2

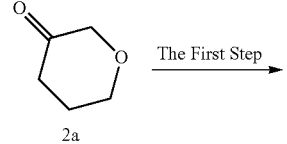

2a

The First Step →

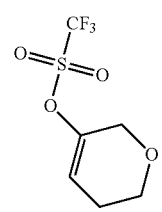

2b

The Second Step →

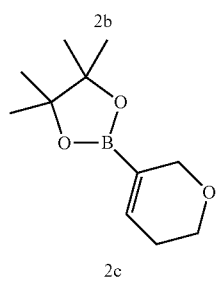

2c

1g
The Third Step →

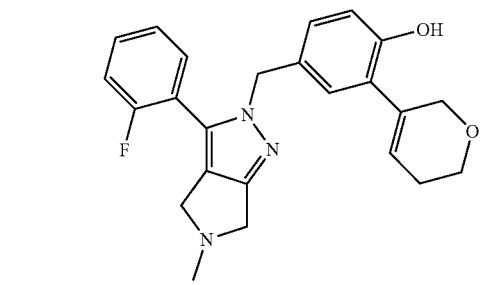

2

The First Step 5,6-dihydro-2H-pyran-3-yl trifluoromethanesulfonate

A 100 mL three-necked flask was taken, and purged with argon for 3 times, lithium diisopropylamide was added into tetrahydrofuran solution (2M, 24 mL, 48.0 mmol), dihydro-2H-pyran-3(4H)-anhydrous tetrahydrofuran solution of ketone 2a (4.0 g, 40.0 mmol) was slowly added under the dry ice acetone bath, after stirring for 30 minutes, N-phenylbis (trifluoromethanesulfonyl)imide anhydrous tetrahydrofuran solution (15.7 g, 44.0 mmol) was slowly added, and after stirring for 1 hour, removing the dry ice acetone bath and stirring overnight at room temperature. After the reaction finished, the reaction solution was quenched by adding ammonium chloride aqueous solution (50 mL), and then extracted with ethyl acetate (100 mL×3). The organic phases were combined and washed with saturated brine (50 mL×3), then dried with anhydrous sodium sulfate, filtered and concentrated. The residue was purified by column chromatography (petroleum ether/ethyl acetate=20/1) to obtain 5. 6-Dihydro-2H-pyran-3-yl triflate 2b (700 mg, colorless oil), yield: 8%. $^1$H NMR (400 MHz, CDCl3) δ 5.93 (s, 1H), 4.16 (s, 2H), 3.77 (t, J=5.2 Hz, 2H), 2.36 (s, 2H).

The Second Step 2-(5, 6-dihydro-2H-pyran-3-yl)-4,4,5,5-tetramethyl-1,3,2-dioxaborane 5,6-dihydro-2H-pyran-3-yl trifluoromethanesulfonate 2b (600 mg, 2.59 mmol), pinacol biborate (788 mg, 3.10 mmol), Potassium acetate (760 mg, 7.76 mmol), [1,1'-bis (diphenylphosphine)ferrocene] dichloropalladium dichloromethane complex (63 mg, 0.0776 mmol) and 1,4-dioxane (25 mL) were added one by one into a 100 mL round bottom flask. The mixture was purged with argon for 3 times, and placed in an 80° C. oil bath for reaction overnight. After the reaction finished, the reaction solution was cooled, poured into water (20 mL), and then extracted with ethyl acetate (50 mL×3). The organic phases were combined and washed with saturated brine (50 mL×3), then dried with anhydrous sodium sulfate, filtered and concentrated. The residue was purified by column chromatography (petroleum ether/ethyl acetate=10/1) to obtain 2-(5,6-Dihydro-2H-pyran-3-yl)-4,4,5,5-tetramethyl-1,3,2-dioxaborane 2c (1.2 g, colorless oil), yield: 60%. 1H NMR (400 MHz, CDCl3) δ 6.66 (s, 1H), 4.25 (s, 2H), 3.78 (t, J=5.3 Hz, 2H), 2.21 (s, 2H), 1.26 (s, 12H).

The Third Step 2-(5,6-dihydro-2H-pyran-3-yl)-4-((3-(2-fluorophenyl)-5-methyl-5,6-dihydropyrrolo[3,4-c]pyrazole-2 (4H)-yl)methyl)phenol 2-bromo-4-((3-(2-fluorophenyl)-5-methyl-5,6-dihydropyrrolo[3,4-c]pyrazole-2(4H)-yl)methyl)phenol 1g (50 mg, 0.125 mmol), 2-(5,6-dihydro-2H-pyran-3-yl)-4,4,5,5-tetramethyl-1,3,2-dioxaborane 2c (39 mg, 0.187 mmol), sodium bicarbonate (21 mg, 0.250 mmol), tris(dibenzylideneacetone) two palladium (11 mg, 0.0125 mmol), 2-bicyclo Hexylphosphine-2',4',6'-triisopropylbiphenyl (12 mg, 0.025 mmol), 1,4-dioxane (2 mL) and water (0.4 mL) were added one by one in a 100 mL round bottom flask. The mixture was purged with argon for 3 times, and placed in an 110° C. oil bath for reaction overnight. After the reaction finished, the reaction solution was cooled, poured into water (2 mL), and then extracted with ethyl acetate (10 mL×3). The organic phase was combined and washed with saturated brine (5 mL×3), then dried with anhydrous sodium sulfate, filtered and concentrated. The residue was purified by a TLC preparation plate (dichloromethane/methanol=10/1) to obtain the target compound 2-(5,6-dihydro-2H-pyran-3-yl)-4-((3-(2-fluorophenyl)-5-methyl-5,6-dihydropyrrolo[3,4-c] pyrazole-2(4H)-yl)methyl)phenol 2 (molecular weight: 405.47, 1.60 mg, white solid), the yield is 3.5%. MS m/z (ESI): 406.4 [M+H]. $^1$H NMR (400 MHz, MeOD) δ7.52-7.49 (m, 1H), 7.38-7.22 (m, 3H), 6.73-6.56 (m, 3H), 5.75 (s, 1H), 5.17 (s, 2H), 4.30 (d, J=1.6 Hz, 2H), 4.08 (s, 2H), 3.97 (s, 2H), 3.80 (t, J=5.6 Hz, 2H), 2.79 (s, 3H), 2.28-2.21 (m, 2H).

Example 3

2-(3-(5,6-dihydro-2H-pyran-3-yl)benzyl)-3-(2-fluorophenyl)-5-methyl-2,4,5,6-tetra hydropyrrolo[3,4-C]pyrazole

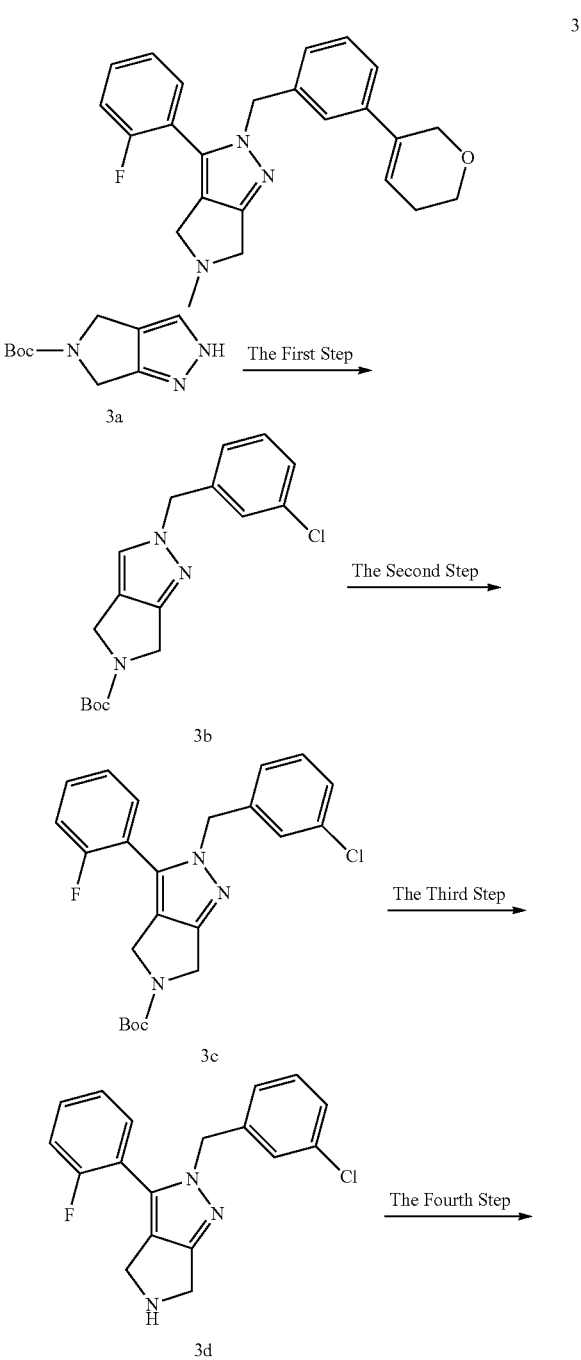

-continued

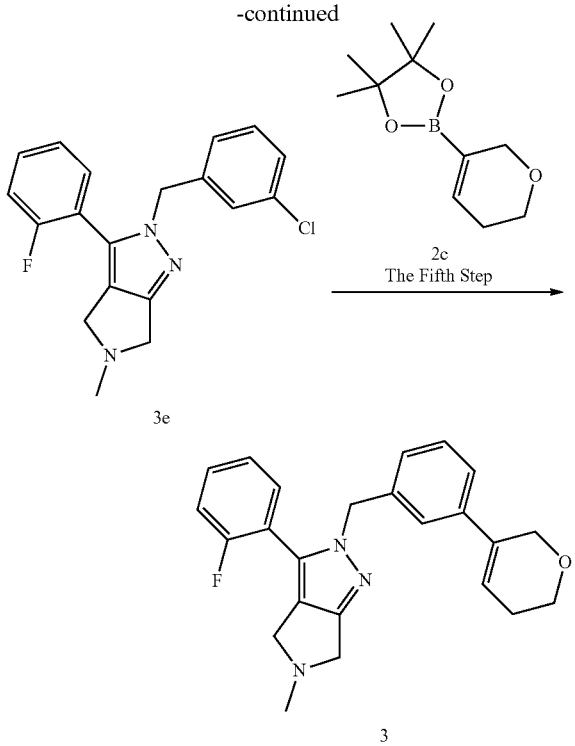

The First Step 2-(3-chlorobenzyl)-2,6-dihydropyrrolo[3,4-c]pyrazole-5(4H)-carboxylic acid tert-butyl ester 2,6-Dihydropyrrolo[3,4-c]pyrazole-5(4H)-carboxylic acid tert-butyl ester 3a (2.8 g, 13.5 mmol) was dissolved in acetonitrile (50 mL), 3-chlorobenzyl bromide (3.3 g, 16.2 mmol) and cesium carbonate (32.5 g, 47 mmol) was added, the mixture was purged with nitrogen for 3 times, and placed in an 80° C. oil bath for 3 hours. The reaction solution was filtered, and the filtrate was concentrated. The residue was purified by column chromatography (petroleum ether:ethyl acetate=2:1) to obtain 2-(3-chlorobenzyl)-2,6-dihydropyrrolo[3,4-c]pyrazole-5(4H)-tert-butyl carboxylate 3b (4.1 g, yellow oil), the yield was 91%. MS m/z (ESI): 334.1 [M+H].

The Second Step 2-(3-chlorobenzyl)-3-(2-fluorophenyl)-2,6-dihydropyrrolo[3,4-c]pyrazole-5(4H)-carboxylic acid tert-butyl ester 2-(3-chlorobenzyl)-2,6-dihydropyrrolo[3,4-c]pyrazole-5 (4H)-carboxylic acid tert-butyl ester 3b (4.6 g, 13.7 mmol), potassium acetate (8 g, 82.2 mmol), allylpalladium(II) chloride dimer (499 mg, 1.37 mmol), N,N-dimethylacetamide (50 mL) and o-fluoroiodobenzene (6.1 g, 27.4 mmol) were added one by one in a round bottom flask. After the oil pump was purged (argon) for four times, the mixture was placed in an oil bath that was heated to 100° C. in advance for reaction for 3 hours. After the reaction was returned to room temperature, the reaction solution was directly poured into water (80 mL), and extracted with ethyl acetate (40 mL×3). The organic phase was washed with brine (40 mL×2), then dried over anhydrous sodium sulfate, filtered and concentrated. The crude product was separated by column chromatography (petroleum ether/ethyl acetate=3/1) to obtain 2-(3-chlorobenzyl)-3-(2-fluorophenyl)-2,6-dihydropyrrolo[3,4-c] pyrazole-5(4H)-tert-butyl carboxylate 3c (1.21 g, yellow oil), yield: 20.6%. MS m/z (ESI): 428.3 [M+H].

The Third Step 2-(3-chlorobenzyl)-3-(2-fluorophenyl)-2,4,5,6-tetrahy dropyrrolo[3,4-c]pyrazole Trifluoroacetic acid (0.5 mL) was added into 2-(3-chlorobenzyl)-3-(2-fluorophenyl)-2,6-dihydropyrrolo[3,4-c] pyrazole-5(4H)-tert-butyl carboxylate 3c (729 mg, 1.45 mmol) in dichloromethane (1.5 mL) solution for reaction at room temperature for 1 hour. After the reaction, the mixture was directly concentrated to obtain the crude product 2-(3-chlorobenzyl)-3-(2-fluorophenyl)-2,4,5,6-tetrahydropyrrolo [3,4-c]pyrazole 3d (581 mg, brown oil), yield: 100%. MS m/z (ESI): 328.2 [M+H].

The Fourth Step 2-(3-chlorobenzyl)-3-(2-fluorophenyl)-5-methyl-2,4,5,6-tetrahydropyrrolo[3,4-c]pyrazole Aqueous formaldehyde solution (37%, 1.2 g, 14.5 mmol) was added into 2-(3-chlorobenzyl)-3-(2-fluorophenyl)-2,4,5,6-tetrahydropyrrolo[3,4-c]Pyrazole 1d (581 mg, 1.45 mmol) in dichloromethane/methanol (6 mL, 2/1) solution, stirred at room temperature for half an hour. Sodium acetate borohydride (1.8 g, 8.7 mmol) was slowly added into the reaction solution for reaction at room temperature overnight. After the reaction solution was concentrated, the mixture was dissolved and diluted with dichloromethane (10 mL), and then washed with ammonia/water (10 mL×2, ⅕) and saturated brine (10 mL) in sequence. The organic phase was dried with anhydrous sodium sulfate and concentrated. 50 mg of crude product was taken and prepared by high pressure liquid chromatography (acetonitrile/water (containing 0.05% trifluoroacetic acid)) to obtain 2-(3-chlorobenzyl)-3-(2-fluorophenyl)-5-methyl-2,4,5,6-Tetrahydropyrrolo[3,4-c]pyrazole 3e (trifluoroacetate, salt coefficient=1.3, 20.1 mg, yellow oil), yield: 24.5%. MSm/z (ESI): 342.8 [M+H].

The Fifth Step 2-(3-(5,6-dihydro-2H-pyran-3-yl)benzyl)-3-(2-fluorophenyl)-5-methyl-2,4,5,6-tetrahydropyrrolo[3,4-C] pyrazole 2-(3-chlorobenzyl)-3-(2-fluorophenyl)-5-methyl-2,4,5,6-tetrahydropyrrolo[3,4-c]Pyrazole 3e (50 mg, 0.147 mmol), (5,6-dihydro-2H-pyran-3-yl)-4,4,5,5-tetramethyl-1,3,2-dioxide Heteroborane 2c (62 mg, 0.294 mmol), sodium bicarbonate (62 mg, 0.735 mmol), tris(dibenzylideneacetone) two palladium (13 mg, 0.0147 mmol), 2-dicyclohexylphosphine-2',4',6'-Triisopropylbiphenyl (14 mg, 0.0294 mmol), 1,4-dioxane (1 mL) and water (0.2 mL) were added one by one into a 25 mL round bottom flask, the mixture was purged with argon for 3 times, and placed in an 110° C. oil bath for reaction overnight. After the reaction finished, the reaction solution was cooled, poured into water (2 mL), and then extracted with ethyl acetate (10 mL×3). The organic phases were combined and washed with saturated brine (5 mL×3), then dried with anhydrous sodium sulfate, filtered and concentrated. The residue was prepared by HPLC (acetonitrile/water (containing 0.05% trifluoroacetic acid) gradient washing) to obtain the target compound 2-(3-(5,6-dihydro-2H-pyran-3-yl)benzyl)-3-(2-fluorophenyl)-5-methyl-2,4,5,6-tetra Hydropyrrolo[3,4-C]pyrazole 3 (trifluoroacetate, salt coefficient=4.0, salt molecular weight: 845.55, 13.1 mg, yellow semi-oil and semi-solid), yield 10.5%. MS m/z (ESI): 390.4 [M+H]. ¹H NMR (400 MHz, MeOD) δ 7.56-7.51 (m, 1H), 7.43-7.37 (m, 1H), 7.33-7.17 (m, 2H), 7.23-7.16 (m, 2H), 6.90 (s, 2H)), 6.11 (s, 1H), 5.34 (s, 2H), 4.62-4.46 (m, 4H), 4.33 (s, 2H), 3.79 (t, J=5.6 Hz, 2H), 3.17 (s, 3H), 2.27 (s, 2H).

Example 4

3-(5,6-dihydro-2H-pyran-3-yl)-5-((3-(2-fluorophenyl)-5-methyl-5,6-dihydropyrrolo[3,4-c]pyrazole-2(4H)-yl)methyl)phenol

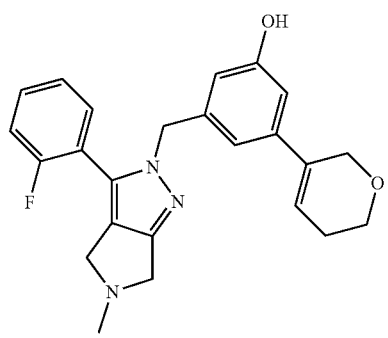
4

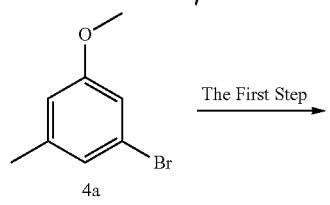
4a
*The First Step*

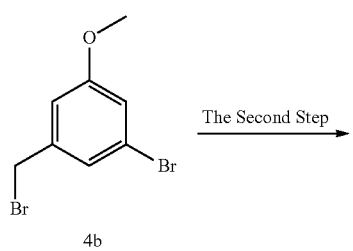
4b
*The Second Step*

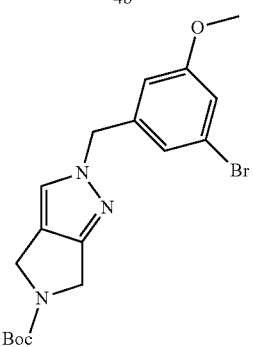
4c
*The Third Step*

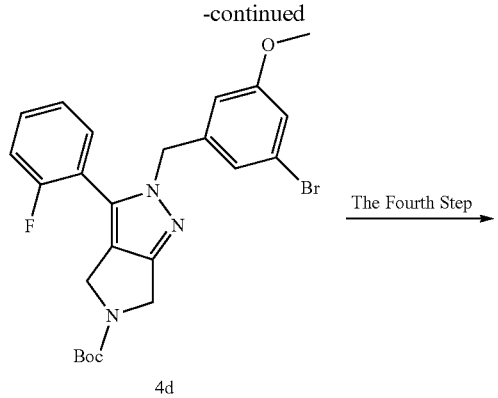
4d
*The Fourth Step*

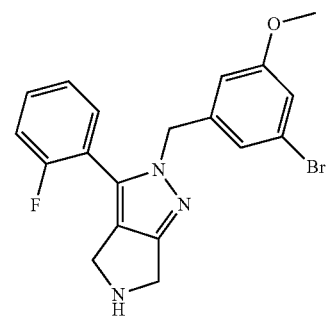
4e
*The Fifth Step*

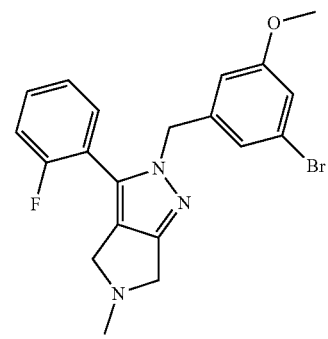
4f
*The Sixth Step*

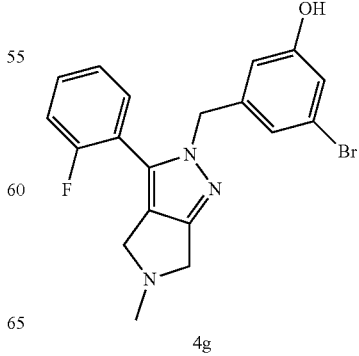 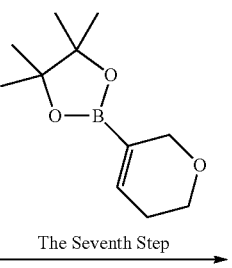
4g
*The Seventh Step*

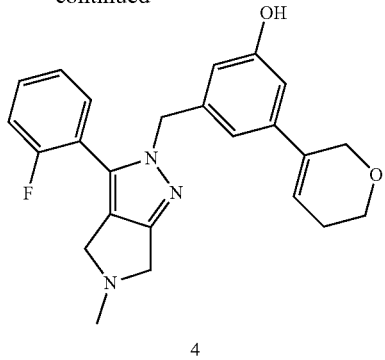

4

The First Step

1-bromo-3-(bromomethyl)-5-methoxybenzene a) bromo-3-methoxy-5-methylbenzene 4a (22.8 g, 113 mmol) was added into a round bottom flask, and dissolved in dichloromethane (100 mL), and N-bromosuccinimide (242 g, 136 mmol) and azobisisobutyronitrile (31.5 g, 192 mmol) were added, heated to 45° C. and refluxed overnight. After the reaction, the reaction was returned to room temperature and extracted with ethyl acetate (40 mL×3). The organic phase was washed successively with water (40 mL×2) and brine (40 mL×2), then dried with anhydrous sodium sulfate, filtered and concentrated. The resulting crude product was separated by normal phase silica gel column (petroleum ether:ethyl acetate=20:1) to obtain 1-bromo-3-(bromomethyl)-5-methoxybenzene 4b (20 g, yellow solid), yield: 63%. MS m/z (ESI): 278.8 [M+H]. $^1$H NMR (400 MHz, CDCl3) δ 7.12 (s, 1H), 6.98 (s, 1H), 6.85 (s, 1H), 4.38 (s, 3H), 3.80 (s, 4H).

The Second Step

2-(3-bromo-5-methoxybenzyl)-2,6-dihydropyrrolo[3,4-c]pyrazole-5(4H)-carboxylic acid tert-butyl ester 2,6-dihydropyrrolo[3,4-c]pyrazole-5(4H)-carboxylic acid tert-butyl ester (12 g, 56.7 mmol) was dissolved in acetonitrile (100 mL), 1-bromo-3-(Bromomethyl)-5-methoxybenzene 4b (19 g, 68.1 mmol), cesium carbonate (64.8 g, 199 mmol) were added, purged with nitrogen for 3 times, and placed in an 80° C. oil bath for 3 hours. The reaction solution was filtered, and the filtrate was concentrated. The residue was purified by column chromatography (petroleum ether:ethyl acetate=2:1) to obtain 2-(3-bromo-5-methoxybenzyl)-2,6-dihydropyrrolo[3,4-c] pyrazole-5(4H)-tert-butyl carboxylate 4c (23 g, yellow oil), yield: 82.9%. MS m/z (ESI): 408.0 [M+H].

The Third Step

2-(3-bromo-5-methoxybenzyl)-3-(2-fluorophenyl)-2,6-dihydropyrrolo[3,4-c]pyrazole-5(4H)-tert-butyl carboxylate 2-(3-Bromo-5-methoxybenzyl)-2,6-dihydropyrrolo[3,4-c]pyrazole-5(4H)-carboxylic acid tert-butyl ester 4c (22 g, 54.1 mmol), potassium acetate (31.8 g, 324.6 mmol), allylpalladium(II) chloride dimer (1.9 mg, 5.41 mmol), N,N-dimethylacetamide (100 mL) and o-fluoroiodobenzene (24 g, 108.2 mmol) were added into a round bottom flask. After the oil pump was purged (argon) for four times, the mixture was placed in an oil bath that was heated to 100° C. in advance for reaction for 3 hours. After the reaction was returned to room temperature, the reaction solution was poured directly into water (80 mL), and extracted with ethyl acetate (40 mL×3). The organic phase was washed sequentially with water (40 mL×2) and brine (40 mL×2), then dried over anhydrous sodium sulfate, filtered and concentrated. The crude product was separated by column chromatography (petroleum ether/ethyl acetate=3/1) to obtain 2-(3-bromo-5-methoxybenzyl)-3-(2-fluorophenyl)-2,6-dihydropyrrolo[3,4-c]pyrazole-5(4H)-carboxylic acid tert-butyl ester 4d (2.7 g, yellow oil), yield: 9.1%. MS m/z (ESI): 502.1 [M+H].

The Fourth Step

2-(3-bromo-5-methoxybenzyl)-3-(2-fluorophenyl)-2,4,5,6-tetrahydropyrrolo[3,4-c]pyrazole Trifluoroacetic acid (7 mL) was added into 2-(3-Bromo-5-methoxybenzyl)-3-(2-fluorophenyl)-2,6-dihydropyrrolo[3,4-c]pyrazole-5(4H)-carboxy solution of tert-butyl ester 4d (2.7 g, 5.5 mmol) in dichloromethane (21 mL) for reaction at room temperature for 1 hour. After the reaction finished, the mixture was directly concentrated to obtain the crude product 2-(3-bromo-5-methoxybenzyl)-3-(2-fluorophenyl)-2,4,5,6-tetrahydropyrrolo[3,4-c]Pyrazole 4e (2.1 g, black liquid), yield: 100%. MS m/z (ESI): 403.2 [M+H].

The Fifth Step

2-(3-bromo-5-methoxybenzyl)-3-(2-fluorophenyl)-5-methyl-2,4,5,6-tetrahydropyrrolo[3,4-c]pyrazole Aqueous formaldehyde solution (37%, 1.39 g, 55 mmol) was added into 2-(3-bromo-5-methoxybenzyl)-3-(2-fluorophenyl)-2,4,5,6-tetrahydro Pyrrolo [3,4-c]pyrazole 4e (2.2 g, 5.5 mmol) in dichloromethane/methanol (20 mL, 2/1) solution and stirred at room temperature for half an hour. Sodium acetate borohydride (6.9 g, 33 mmol) was slowly added into the reaction solution for reaction at room temperature overnight. After the reaction solution was concentrated, the mixture was dissolved and diluted with dichloromethane (10 mL), and then washed with ammonia water/water (10 mL×2, ⅓) and saturated brine (10 mL) in turn. The organic phase was dried with anhydrous sodium sulfate and concentrated to obtain a crude product. 50 mg of crude product was taken and prepared by high pressure liquid chromatography (acetonitrile/water (containing 0.05% trifluoroacetic acid)) to obtain 2-(3-bromo-5-methoxybenzyl)-3-(2-fluorophenyl)-5-Methyl-2,4,5,6-tetrahydropyrrolo[3,4-c]pyrazole 4f (trifluoroacetate, salt coefficient=2, 4.1 mg, yellow oil), yield: 5.1%. MS m/z (ESI): 416.3 [M+H]. $^1$H NMR (400 MHz, CDCl3) δ7.49 (s, 2H), 7.25 (s, 2H), 6.95 (s, 1H), 6.77 (s, 1H), 6.50 (s, 1H), 5.20 (s, 2H), 5.01 (s, 2H), 4.22-3.97 (m, 2H), 3.73 (s, 3H), 3.16 (s, 3H).

The Sixth Step

3-bromo-5-((3-(2-fluorophenyl)-5-methyl-5,6-dihydropyrrolo[3,4-c]pyrazole-2(4H)-yl)Methyl)phenol 2-(3-bromo-5-methoxybenzyl)-3-(2-fluorophenyl)-5-methyl-2,4,5,6-tetrahy dropyrrolo[3,4-c]Pyrazole 4f (6 g, 14.5 mmol) was weighed and then put into an round bottom flask, dichloromethane (10 mL) was added, and boron tribromide (12 mL) was added under ice bath for reaction for 2 hours. After the reaction finished, the mixture was quenched with water (10 mL) and extracted with dichloromethane (15 mL×3). The organic phase was washed with brine (10 mL×2), then dried over anhydrous sodium sulfate, filtered and concentrated. 50 mg of the crude product obtained was prepared by high pressure liquid chromatography (acetonitrile/water (containing 0.05% trifluoroacetic acid)) to obtain 3-bromo-5-((3-(2-Fluorophenyl)-5-methyl-5,6-dihydropyrrolo[3,4-c]pyrazole-2(4H)-yl)methyl)phenol 4g (Trifluoroacetate, salt coefficient=1.7, 23 mg, light yellow oil), yield: 30.5%. MS m/z (ESI): 404.2 [M+H]. $^1$H NMR (400 MHz, MeOD) δ 7.58-7.53 (m, 1H), 7.40-7.26 (m, 2H), 6.80 (s, 1H), 6.56 (s, 1H), 6.39 (s, 1H), 5.24 (s, 2H), 4.60 (s, 4H)), 3.18 (s, 3H).

The Seventh Step

3-(5,6-dihydro-2H-pyran-3-yl)-5-((3-(2-fluorophenyl)-5-methyl-5,6-dihydropyrrolo[3,4-c]pyrazole-2(4H)-yl)methyl)phenol 3-bromo-5-((3-(2-fluorophenyl)-5-methyl-5,6-dihydropyrrolo[3,4-c]pyrazole-2(4H)-yl)methyl) Phenol 4g (50 mg, 0.125 mmol), (5,6-dihydro-2H-pyran-3-yl)-4,4,5,5-tetramethyl-1,3,2-dioxaboron Alkane 2c (53 mg, 0.250 mmol), sodium bicarbonate (21 mg, 0.250 mmol), tris(dibenzylideneacetone)dipalladium (11 mg, 0.0125 mmol), 2-dicyclohexylphosphine-2',4',6'-Triisopropylbiphenyl (12 mg, 0.0250 mmol), 1,4-dioxane (2 mL) and water (0.4 mL) were added one by one into a 25 mL round bottom flask, the mixture was purged with argon for 3 times and placed in an 110° C. oil bath for reaction overnight. After the reaction, the reaction solution was cooled, poured into water (2 mL), and then extracted with ethyl acetate (10 mL*3). The organic phases were combined and washed with saturated brine (5 mL*3), then dried with anhydrous sodium sulfate, filtered and concentrated. The residue was prepared by HPLC (acetonitrile/water (containing 0.05% trifluoroacetic acid) gradient washing) to obtain the target compound 3-(5,6-dihydro-2H-pyran-3-yl)-5-((3-(2-fluorophenyl)-5-methyl-5,6-dihydropyrrolo[3,4-c]pyrazole-2(4H)-yl)methyl)phenol 4 (trifluoroacetate, salt coefficient=1.7, salt molecular weight: 599.29, 4.9 mg, white solid), yield: 10%. MS m/z (ESI): 406.4 [M+H]. $^1$H NMR (400 MHz, MeOD) δ 7.57-7.53 (m, 1H), 7.43-7.36 (m, 1H), 7.35-7.26 (m, 2H), 6.60 (s, 1H), 6.36 (s, 2H), 6.07 (s, 1H), 5.26 (s, 2H), 5.01 (s, 2H), 4.63-4.59 (m, 2H), 4.28 (s, 2H), 3.77 (t, J=5.6 Hz, 2H), 3.17 (s, 3H), 2.25 (s, 2H).

Example 5

2-(3-(3,6-dihydro-2H-pyran-4-yl)benzyl)-3-(2-fluorophenyl)-5-methyl-2,4,5,6-Tetrahy dropyrrolo[3,4-C]pyrazole

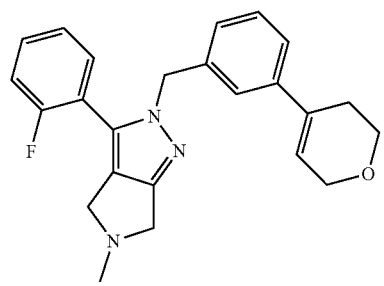

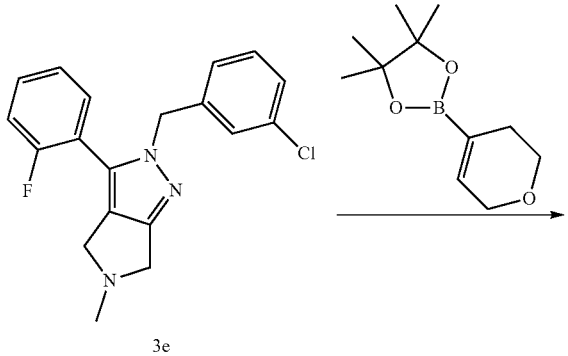

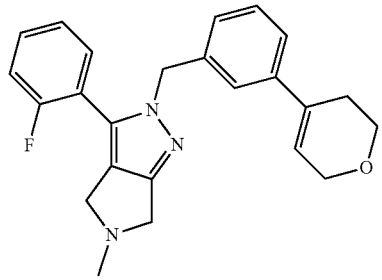

2-(3-Chlorobenzyl)-3-(2-fluorophenyl)-5-methyl-2,4,5,6-tetrahydropyrrolo[3,4-c]pyrazole 3e (50 mg, 0.147 mmol), 2-(3,6-dihydro-2H-pyran-4-yl)-4,4,5,5-tetramethyl-1,3,2-dioxaborane (62 mg, 0.294 mmol), sodium bicarbonate (62 mg, 0.735 mmol), tris(dib enzylideneacetone)dipalladium (13 mg, 0.0147 mmol), 2-dicyclohexylphosphine-2',4',6'-triisopropyl Biphenyl (14 mg, 0.0294 mmol), 1,4-dioxane (1 mL) and water (0.2 mL) were added one by one into 25 ml round bottom flask, the mixture was purged with argon for 3 times, and placed in an 110° C. oil bath for reaction overnight. After the reaction, the reaction solution was cooled, poured into water (2 mL), and then extracted with ethyl acetate (10 mL'3). The organic phases were combined and washed with saturated brine (5 mL×3), then dried with anhydrous sodium sulfate, filtered and concentrated. The residue was prepared by HPLC (acetonitrile/water (containing 0.05% trifluoroacetic acid) gradient washing) to obtain the target compound 2-(3-(3,6-dihydro-2H-pyran-4-yl)benzyl)-3-(2-fluorophenyl)-5-methyl-2,4,5,6-tetra Hydropyrrolo[3,4-C]pyrazole 5 (trifluoroacetate, salt coefficient=4.0, salt molecular weight: 845.55, 13.1 mg, yellow semi-oil and semi-solid), yield 10.5%. MS m/z (ESI): 390.4 [M+H]. $^1$H NMR (400 MHz, CDCl3) δ7.47 (d, J=6.8 Hz, 1H), 7.30-7.18 (m, 4H), 7.07 (s, 1H), 6.93-6.91 (d, J=6.8 Hz, 1H), 6.05 (s, 1H), 4.97 (s, 2H), 5.28-5.26 (d, J=8.8 Hz, 2H), 4.97 (dd, J=12.8 Hz, 1H), 4.10-4.00 (m, 2H), 3.92-3.90 (m, 2H), 3.12 (s, 2H), 2.34 (s, 2H).

Example 6

2-(3-chloro-5-(3,6-dihydro-2H-pyran-4-yl)benzyl)-3-(2-fluorophenyl)-5-methyl-2,4,5,6-tetrahydropyrrolo[3,4-c]pyrazole

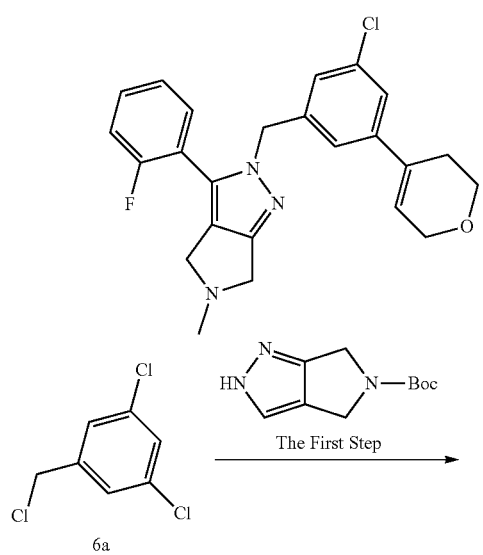

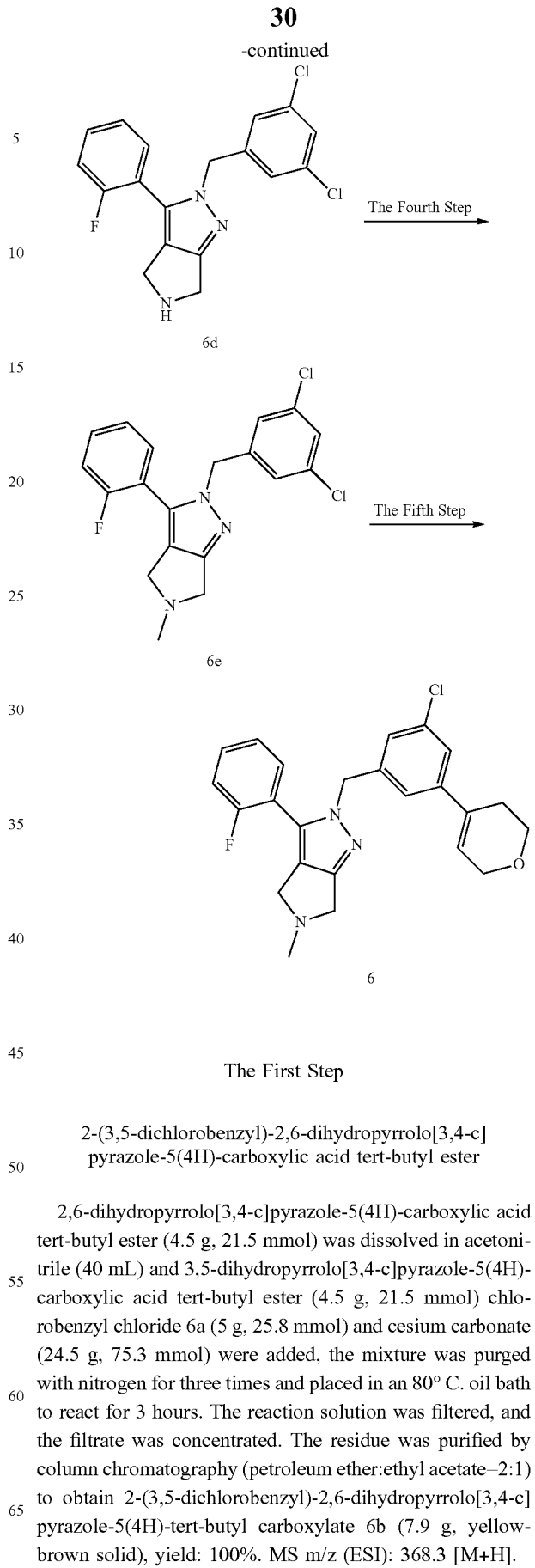

The First Step 2-(3,5-dichlorobenzyl)-2,6-dihydropyrrolo[3,4-c]pyrazole-5(4H)-carboxylic acid tert-butyl ester 2,6-dihydropyrrolo[3,4-c]pyrazole-5(4H)-carboxylic acid tert-butyl ester (4.5 g, 21.5 mmol) was dissolved in acetonitrile (40 mL) and 3,5-dihydropyrrolo[3,4-c]pyrazole-5(4H)-carboxylic acid tert-butyl ester (4.5 g, 21.5 mmol) chlorobenzyl chloride 6a (5 g, 25.8 mmol) and cesium carbonate (24.5 g, 75.3 mmol) were added, the mixture was purged with nitrogen for three times and placed in an 80° C. oil bath to react for 3 hours. The reaction solution was filtered, and the filtrate was concentrated. The residue was purified by column chromatography (petroleum ether:ethyl acetate=2:1) to obtain 2-(3,5-dichlorobenzyl)-2,6-dihydropyrrolo[3,4-c]pyrazole-5(4H)-tert-butyl carboxylate 6b (7.9 g, yellow-brown solid), yield: 100%. MS m/z (ESI): 368.3 [M+H].

The Second Step 2-(3,5-dichlorobenzyl)-3-(2-fluorophenyl)-2,6-dihydropyrrolo[3,4-c]pyrazole-5(4H)-carboxy tert-butyl ester 2-(3,5-dichlorobenzyl)-2,6-dihydropyrrolo[3,4-c]pyrazole-5(4H)-carboxylic acid tert-butyl ester 6b(7.9 g, 21.5 mmol), potassium acetate (12.6 g, 129.0 mmol), allyl palladium(II) chloride dimer (782 mg, 2.2 mmol), N,N-dimethylacetamide (30 mL) and ortho fluoriodobenzene (9.5 g, 43.0 mmol) were added one by one into an round bottom flask. After the oil pump was purged (argon) for four times, the mixture was placed in an oil bath that was heated to 100° C. in advance for reaction for 3 hours. After the reaction was returned to room temperature, the reaction solution was poured directly into water (40 mL), and extracted with ethyl acetate (40 mL×3). The organic phase was washed sequentially with water (40 mL×2) and brine (40 mL×2), then dried over anhydrous sodium sulfate, filtered and concentrated. The obtained crude product was separated by column chromatography (petroleum ether/ethyl acetate=5/1) to obtain 2-(3,5-dichlorobenzyl)-3-(2-fluorophenyl)-2,6-dihydropyrrolo[3,4-c]pyrazole-5(4H)-carboxylic acid tert-butyl ester 6c (4.8 g, yellow oil), yield: 48.3%. MS m/z (ESI): 462.3 [M+H].

The Third Step 2-(3,5-dichlorobenzyl)-3-(2-fluorophenyl)-2,4,5,6-tetrahydropyrrolo[3,4-c]pyrazole Trifluoroacetic acid (7 mL) was added into 2-(3,5-Dichlorobenzyl)-3-(2-fluorophenyl)-2,6-dihydropyrrolo[3,4-c]pyrazole-5(4H)-carboxylic acid tert-butyl ester 6c (4.8 g, 10.4 mmol) in dichloromethane (12 mL) for reaction at room temperature for 1 hour. After the reaction finished, the crude product 2-(3,5-dichlorobenzyl)-3-(2-fluorophenyl)-2,4,5,6-tetrahydropyrrolo[3,4-c]pyrazole 6d (3.76 g, black liquid) was obtained by directly concentrated, yield: 100%. MS m/z (ESI): 362.2 [M+H].

The Fourth Step 2-(3,5-dichlorobenzyl)-3-(2-fluorophenyl)-5-methyl-2,4,5,6-tetrahydropyrrolo[3,4-c]pyrazole Aqueous formaldehyde solution (37%, 7.3 g, 104.0 mmol) was added into 2-(3,5-dichlorobenzyl)-3-(2-fluorophenyl)-2,4,5,6-tetrahydropyrrolo[3,4-c]pyrazole 6d (3.76 mg, 10.4 mmol) in dichloromethane/methanol (30 mL, 2/1) solution, stirred at room temperature for half an hour. Sodium acetate borohydride (6.6 g, 71.3 mmol) was slowly added into the reaction solution for reaction at room temperature overnight. After the reaction solution was concentrated, the mixture was dissolved and diluted with dichloromethane (10 mL), and then washed with ammonia/water (10 mL×2, 1/5) and saturated brine (10 mL) in turn. The organic phase was dried with anhydrous sodium sulfate and concentrated to obtain a crude product. 50 mg of crude product was taken and prepared by high pressure liquid chromatography (acetonitrile/water (containing 0.05% trifluoroacetic acid)) to obtain 2-(3,5-dichlorobenzyl)-3-(2-fluorophenyl)-5-methyl-2,4,5,6-tetrahydropyrrolo[3,4-c]pyrazole 6f (trifluoroacetate, salt coefficient=1.7, 16.2 mg, yellow solid), yield 21.6%. MS m/z (ESI): 376.3 [M+H]. $^1$H NMR (400 MH, CDCl3) δ 7.50 (d, J=5.6 Hz, 1H), 7.27 (s, 2H), 7.26-7.17 (m, 2H), 6.94 (s, 2H), 5.19 (s, 2H), 4.97 (s, 2H), 4.10-4.02 (m, 2H), 3.12 (s, 3H).

The Fifth Step 2-(3-chloro-5-(3,6-dihydro-2H-pyran-4-yl)benzyl)-3-(2-fluorophenyl)-5-methyl-2,4,5,6-tetrahydropyrrolo[3,4-c]pyrazole (3,5-dichlorobenzyl)-3-(2-fluorophenyl)-5-methyl-2,4,5,6-tetrahydropyrrolo[3,5-dichlorobenzyl)-3-(2-fluorophenyl)-5-methyl-2,4,5,6-tetrahydropyrrolo[3,4-c] pyrazole 6f (300 mg, 0.8 mmol), potassium carbonate (138 mg, 1.6 mmol), tris(dibenzylideneacetone)dipalladium (73 mg, 0.08 mmol), 2-dicyclohexylphosphine-2',4',6'-triisopropylbiphenyl (76 mg, 0.16 mmol), 1,4-dioxane (3 mL), water (1 mL) and 3,6-dihydropyran-4-borate (210 mg, 1.0 mmol) were added one by one into an round bottom flask, the oil pump was purged (argon) for four times, and then placed in an oil bath that was raised to 110° C. in advance for reaction for 16 hours. After the reaction was returned to room temperature, the reaction solution was poured directly into water (20 mL), and extracted with ethyl acetate (20 mL×3). The organic phase was washed with brine (10 mL×2), then dried over anhydrous sodium sulfate, filtered and concentrated. The obtained crude product was separated by a preparation plate (dichloromethane: methanol=10:1) to obtain the target compound 2-(3-chloro-5-(3,6-dihydro-2H-pyran-4-yl)benzyl)-3-(2-fluorophenyl)-5-methyl-2,4,5,6-tetrahydropyrrolo[3,4-c]pyrazole 6 (53.0 mg, yellow oil), yield: 15.6%. MS m/z (ESI): 424.4 [M+H]. 1H NMR (400 MHz, CDCl3) δ 7.42-7.30 (m, 1H), 7.26-7.16 (m, 4H), 6.91 (d, J=11.2 Hz, 2H), 6.05 (s, 1H), 5.20 (s, 2H), 4.29 (d, J=4.2 Hz, 2H), 4.07 (s, 2H), 3.97 (s, 2H), 3.87 (t, J=5.6 Hz, 2H), 2.78 (s, 3H), 2.38 (s, 2H).

Example 7

2-(3-(3,6-dihydro-2H-pyran-4-yl)-4-fluorobenzyl)-3-(2-fluorophenyl)-5-methyl-2,4,5,6-tetrahydropyrrolo[3,4-c]pyrazole

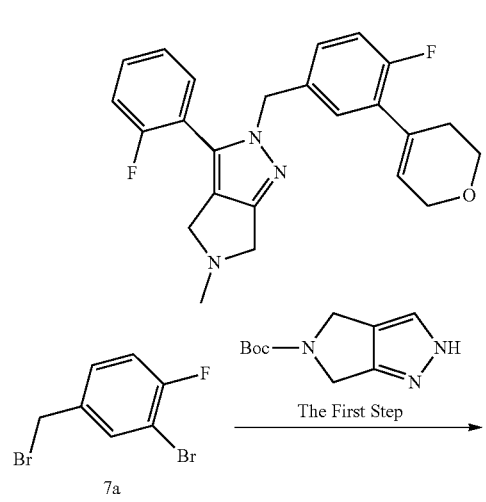

7

The First Step

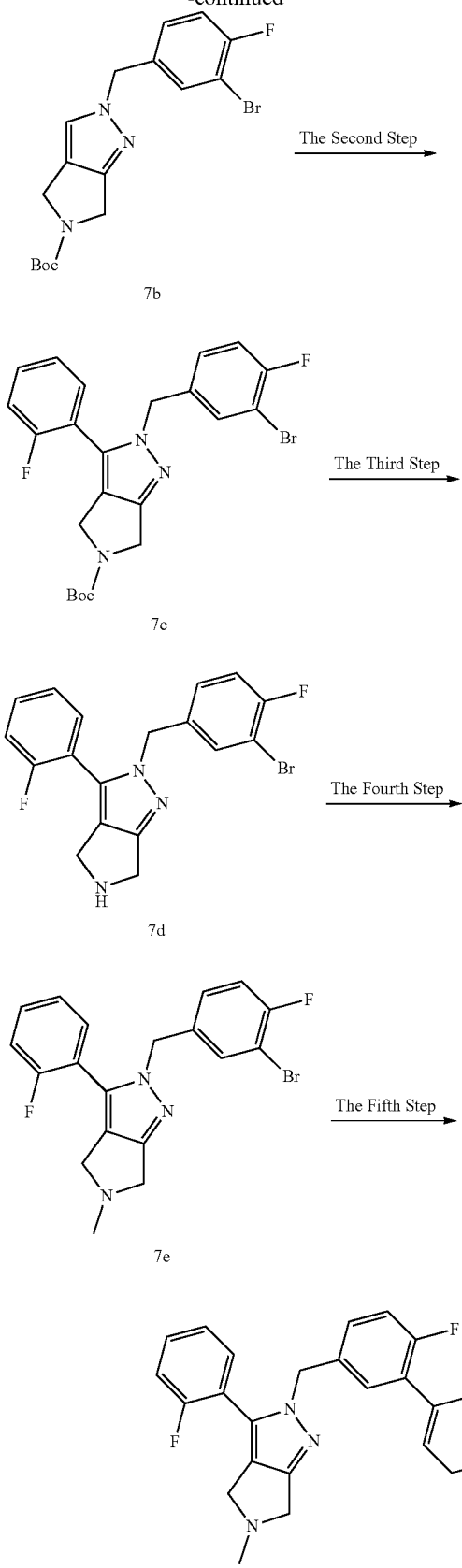

The First Step 2-(3-bromo-4-fluorobenzyl)-2,6-dihydropyrrolo[3,4-c]pyrazole-5(4H)-carboxylic acid tert-butyl ester 2,6-dihydropyrrolo[3,4-c]pyrazole-5(4H)-carboxylic acid tert-butyl ester (3.3 g, 15.8 mmol) was dissolved in acetonitrile (40 mL), and 3-bromo-4-Fluorobenzyl bromide 7a (5 g, 18.9 mmol) and cesium carbonate (18 g, 55.3 mmol) were added, the mixture was purged with nitrogen for 3 times, and placed in an 80° C. oil bath for 3 hours. The reaction solution was filtered, and the filtrate was concentrated. The residue was purified by column chromatography (petroleum ether: ethyl acetate=2:1) to obtain 2-(3-bromo-4-fluorobenzyl)-2,6-dihydropyrrolo[3,4-c]pyrazole-5(4H)-tert-butyl carboxylate 7b (6.1 g, yellow solid), yield: 97.7%. MS m/z (ESI): 396.0 [M+H].

The Second Step 2-(3-bromo-4-fluorobenzyl)-3-(2-fluorophenyl)-2,6-dihydropyrrolo[3,4-c]pyrazole-5(4H)-tert-butyl carboxylate 2-(3-bromo-4-fluorobenzyl)-2,6-dihydropyrrolo[3,4-c]pyrazole-5(4H)-carboxylic acid tert-butyl ester 7b (6.1 g, 15.4 mmol), potassium acetate (9 g, 92.4 mmol), allyl palladium(II) chloride dimer (560 mg, 1.54 mmol), N,N-dimethylacetamide (30 mL) and ortho fluoriodobenzene (6.8 g, 30.8 mmol) were added into a round bottom flask one by one. After the oil pump was purged (argon) for four times, the mixture was placed in an oil bath that was raised to 100° C. in advance for reaction for 3 hours. After the reaction was returned to room temperature, the reaction solution was poured directly into water (80 mL), and extracted with ethyl acetate (40 mL×3). The organic phase was washed sequentially with water (15 mL×2) and brine (15 mL×2), then dried over anhydrous sodium sulfate, filtered and concentrated. The obtained crude product was separated by column chromatography (petroleum ether/ethyl acetate=5/1) to obtain 2-(3-bromo-4-fluorobenzyl)-3-(2-fluorophenyl)-2,6-dihydro Pyrrolo[3,4-c]pyrazole-5(4H)-tert-butyl carboxylate 7c (1.1 g, yellow-brown oil), yield: 14.6%. MS m/z (ESI): 492.2 [M+H].

The Third Step 2-(3-bromo-4-fluorobenzyl)-3-(2-fluorophenyl)-2,4,5,6-tetrahydropyrrolo[3,4-c]pyrazole trifluoroacetic acid (4 mL) was added into 2-(3-bromo-4-fluorobenzyl)-3-(2-fluorophenyl)-2,6-dihydropyrrolo[3,4-c]pyrazole-5(4H)-tert-butyl carboxylate 7c (1.1 g, 2.25 mmol) in dichloromethane (12 mL) solution at room temperature for 1 hour. After the reaction finished, the crude product 2-(3-bromo-4-fluorobenzyl)-3-(2-fluorophenyl)-2,4,5,6-tetrahydropyrrolo[3,4-c]pyrazole 7d (875 mg, black liquid) was obtained by directly concentrated, yield: 100%. MS m/z (ESI): 392.2 [M+H].

The Fourth Step 2-(3-bromo-4-fluorobenzyl)-3-(2-fluorophenyl)-5-methyl-2,4,5,6-tetrahydropyrrolo[3,4-c]pyrazole Aqueous formaldehyde solution (37%, 1.6 g, 22.5 mmol) was added into 2-(3-bromo-4-fluorobenzyl)-3-(2-fluorophenyl)-2,4,5,6-tetrahydropyrrolo[3,4-c]pyrazole 7d (875 mg, 2.25 mmol) in dichloromethane/methanol (15 mL, 2/1) solution, stirred at room temperature for half an hour. Sodium acetate borohydride (1.4 g, 6.75 mmol) was slowly added into the reaction solution for reaction at room temperature overnight. After the reaction solution was concentrated, the mixture was dissolved and diluted with dichloromethane (10 mL), and then washed with ammonia/water (10 mL×2, ⅓) and saturated brine (10 mL) in turn. The organic phase was dried with anhydrous sodium sulfate and concentrated to obtain a crude product. 50 mg of crude product was taken and prepared by high pressure liquid chromatography (acetonitrile/water (containing 0.05% trifluoroacetic acid)) to obtain 2-(3-bromo-4-fluorobenzyl)-3-(2-fluorophenyl)-5-methyl-2,4,5,6-tetrahydropyrrolo[3,4-c] pyrazole 7e (trifluoroacetate, salt coefficient=2.3, 16.2 mg, pale yellow solid), yield: 19.0%. MS m/z (ESI): 406.3 [M+H]. $^1$H NMR (400 MHz, CDCl3) δ 7.42 (d, J=5.6 Hz, 1H), 7.22-7.11 (m, 4H), 6.96 (t, J=8.0 Hz, 1H), 6.89 (s, 1H), 5.13 (s, 2H), 4.89 (s, 2H), 4.05 (s, 2H), 3.05 (s, 3H).

The Fifth Step 2-(3-(3,6-dihydro-2H-pyran-4-yl)-4-fluorobenzyl)-3-(2-fluorophenyl)-5-methyl-2,4,5,6-tetrahydropyrrolo[3,4-c]pyrazole 2-(3-bromo-4-fluorobenzyl)-3-(2-fluorophenyl)-5-methyl-2,4,5,6-tetrahydropyrrolo[3,4-c]pyrazole 7e (400 mg, 1.0 mmol), sodium bicarbonate (168 mg, 2.0 mmol), tris(dibenzylideneacetone) two palladium (91 mg, 0.1 mmol), 2-dicyclohexylphosphine-2',4',6'-triisopropylbiphenyl (95 mg, 0.2 mmol), 1,4-dioxane (5 mL), water (1 mL) and 3,6-dihydropyran-4- The borate ester (420 mg, 2.0 mmol) were added into a round bottom flask one by one, the mixture was purged (argon) by the oil pump for four times and then put into an oil bath which was raised to 110° C. in advance for reaction for 16 hours. After the reaction was returned to room temperature, the reaction solution was poured directly into water (20 mL), and extracted with ethyl acetate (20 mL×3). The organic phase was washed with brine (10 mL×2), then dried over anhydrous sodium sulfate, filtered and concentrated. The obtained crude product was prepared by high pressure liquid chromatography (acetonitrile/water (containing 0.05% trifluoroacetic acid) to obtain 2-(3-(3,6-dihydro-2H-pyran-4-yl)-4-fluorobenzyl)-3-(2-fluorophenyl)-5-methyl-2,4,5,6-tetrahydropyrrolo[3,4-c] pyrazole 7 (trifluoroacetate, salt coefficient=0.3, 60 mg, yellow solid), yield 13.5%. MS m/z (ESI): 408.4 [M+H]. $^1$H NMR (400 MHz, CDCl3) δ7.44-7.42 (m, 1H), 7.26-7.16 (m, 3H), 6.94-6.86 (m, 3H), 5.94 (s, 1H), 5.20 (s, 2H), 4.29 (s, 2H), 4.13 (s, 2H), 4.02 (s, 2H), 3.86 (s, 2H), 2.83 (s, 3H), 2.41 (s, 2H).

Example 8

3-(3,6-dihydro-2H-pyran-4-yl)-5-((3-(2-fluorophenyl)-5-methyl-5,6-dihydropyrrolo[3,4-c]pyrazole-2(4H)-yl)methyl)phenol

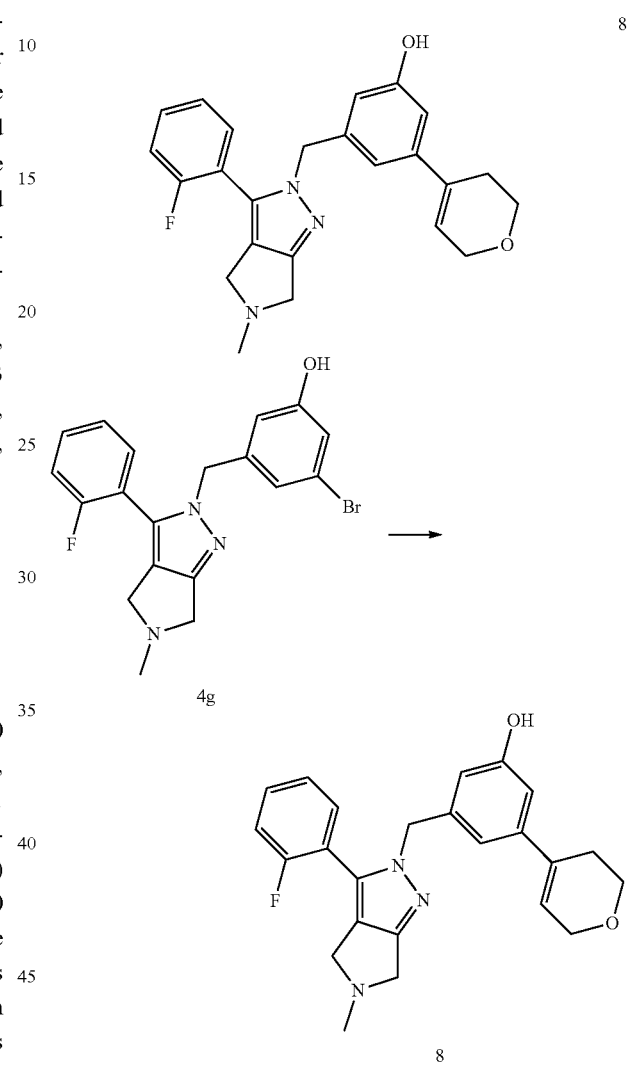

3-bromo-5-((3-(2-fluorophenyl)-5-methyl-5,6-dihydro-pyrrolo[3,4-c]pyrazole-2(4H)-yl)methyl) Phenol 4g (300 mg, 0.75 mmol), sodium bicarbonate (126 mg, 1.5 mmol), tris(dibenzylideneacetone)dipalladium (68 mg, 0.075 mmol), 2-dicyclohexylphosphine-2',4',6'-triisopropylbiphenyl (71 mg, 0.15 mmol), 1,4-dioxane (5 mL), water (1 mL) and 3,6-dihydropyran-4-borate (315 mg, 1.5 mmol) were added to a round bottom flask one by one, the mixture was purged (argon) by the oil pump for four times, and was put in an oil bath that was raised to 110° C. in advance for reaction for 16 hours. After the reaction was returned to room temperature, the reaction solution was poured directly into water (20 mL), and extracted with ethyl acetate (20 mL×3). The organic phase was washed with brine (10 mL×2), then dried over anhydrous sodium sulfate, filtered and concentrated. The obtained crude product was prepared by high pressure liquid chromatography (acetonitrile/water (containing 0.05% trifluoroacetic acid)) to obtain the target compound 3-(3,6-dihydro-2H-pyran-4-yl)-5-((3-(2-fluorophenyl)-5-methyl-5,6-dihydropyrrolo[3,4-c]pyrazole-2 (4H)-yl)methyl)phenol 8 (trifluoroacetate, salt coefficient=1.5, 80.3 mg, yellow solid), yield: 18.5%. MS m/z (ESI): 406.4 [M+H]. ¹H NMR (400 MHz, CDCl3) δ7.46-7.40 (m, 1H), 7.26-7.15 (m, 4H), 6.76 (s, 1H), 6.60 (s, 1H), 6.07 (s, 1H), 6.07 (s, 1H), 5.34-5.18 (m, 2H), 4.94-4.84 (m, 2H), 4.28 (d, J=6.0 Hz, 2H), 4.15-4.06 (m, 2H), 3.89 (t, J=5.6 Hz, 2H), 3.12 (s, 3H), 2.40 (s, 2H).

Example 9

3-(2-fluorophenyl)-5-methyl-2-(3-(1,2,3,6-tetrahydropyridin-4-yl)benzyl)-2,4,5,6-tetrahydropyrrolo[3,4-C]pyrazole

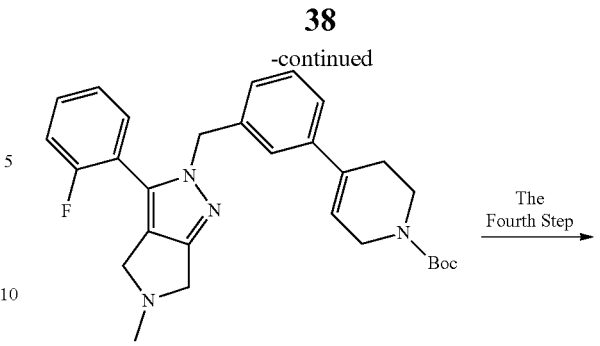

9d

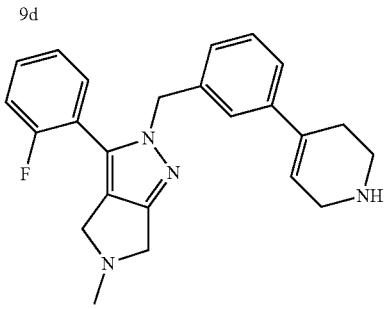

9

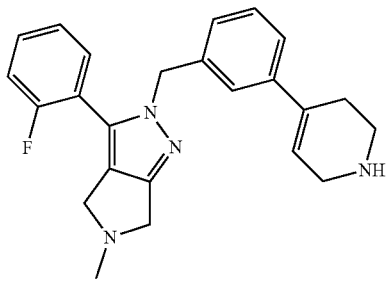

9a

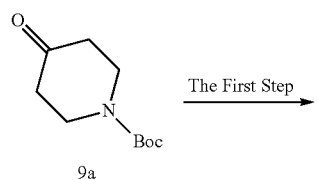

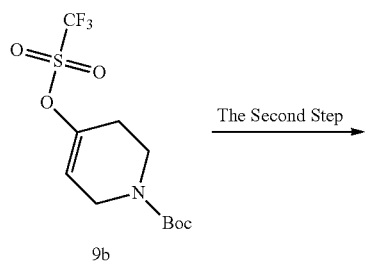

9b

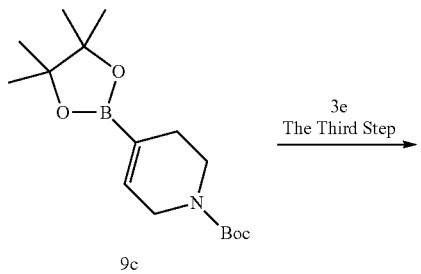

9c

The First Step 4-(((trifluoromethyl)sulfonyl)oxy)-3,6-dihydropyridine-1(2H)-carboxylic acid tert-butyl ester A 100 mL three-necked flask was taken, and purged with argon for 3 times, and lithium diisopropylamide was added into tetrahydrofuran solution (2M, 15.1 mL, 30.2 mmol) in dry ice acetone bath, N-tert-butoxycarbonyl-4-piperidone 9a anhydrous tetrahydrofuran solution (5.00 g, 25.1 mmol) was slowly added, stirred for 1 hour, N-phenylbis(trifluoromethanesulfonyl)imide anhydrous tetrahydrofuran solution (9.90 g, 27.6 mmol) was slowly added, stirred for 1 After hours, the dry ice acetone bath was removed, then stirred overnight at room temperature. After the reaction finished, the reaction solution was quenched with aqueous ammonium chloride solution (50 mL), and then extracted with ethyl acetate (100 mL×3). The organic phases were combined and washed with saturated brine (50 mL×3), then dried with anhydrous sodium sulfate, filtered and concentrated. The residue was purified by column chromatography (petroleum ether/ethyl acetate=10/1) to obtain 4-(((Trifluoromethyl) sulfonyl)oxy)-3,6-dihydropyridine-1(2H)-carboxylic acid tert-butyl ester 9b (6.1 g, colorless oil), yield: 73%. ¹H NMR (400 MHz, CDCl3) δ 5.75 (s, 1H), 4.06-4.02 (m, 2H), 3.62 (t, J=6.0 Hz, 2H), 2.43 (s, 2H), 1.47 (s, 9H)).

The Second Step 4-(4,4,5,5-tetramethyl-1,3,2-dioxaborolan-2-yl)-3,6-dihydropyridine-1(2H)-tert-butyl carboxylate (((trifluoromethyl)sulfonyl)oxy)-3,6-dihydropyridine-1 (2H)-carboxylic acid tert-butyl ester 9b (6.1 g, 18.4 mmol), pinacol diborate (5.6 g, 22.1 mmol), potassium acetate (5.4 g, 55.3 mmol), [1,1'-bis(diphenylphosphine)ferrocene] palladium dichloride dichloromethane complex (452 mg, 0.553 mmol)) and 1,4-dioxane (100 mL) were added into a 100 mL round bottom flask one by one, the mixture was purged with argon for three times, and placed in an 80° C. oil bath for reaction overnight. After the reaction finished, the reaction solution was cooled, poured into water (50 mL), and then extracted with ethyl acetate (100 mL×3). The organic phase was combined and washed with saturated brine (50 mL×3), then dried with anhydrous sodium sulfate, filtered and concentrated. The residue was purified by column chromatography (petroleum ether/ethyl acetate=5/1) to obtain 4-(4,4,5,5-tetramethyl-1,3,2-dioxaborolan-2-yl)-3,6-dihydropyridine-1(2H)-carboxylic acid tert-butyl ester 9c (3.0 g, colorless oil), yield: 53%. $^1$H NMR (400 MHz, CDCl3) δ 6.45 (s, 1H), 3.97-3.91 (m, 2H), 3.42 (t, J=5.6 Hz, 2H), 2.21 (s, 2H), 1.45 (s, 9H)), 1.28 (s, 6H), 1.24 (s, 6H).

The Third Step 4-(3-((3-(2-fluorophenyl)-5-methyl-5,6-dihydropyrrolo[3,4-c]pyrazole-2(4H)-yl) (methyl)phenyl)-3-tert-butyl ester, 1,6-dihydropyridine-1(2H)-carboxylic acid tert-butyl ester 2-(3-chlorobenzyl)-3-(2-fluorophenyl)-5-methyl-2,4,5,6-tetrahydropyrrolo[3,4-c]pyrazole 3e (600 mg, 1.76 mmol), 4-(4,4,5,5-tetramethyl-1,3,2-dioxaborolan-2-yl)-3,6-dihydropyridine-1(2H)-tert-butyl carboxylate 9c (1.1 g, 3.52 mmol), sodium bicarbonate (739 mg, 8.80 mmol), tris (dibenzylideneacetone) two palladium (161 mg, 0.176 mmol), 2-dicyclohexylphosphine-2',4',6'-triisopropylbiphenyl (168 mg, 0.352 mmol), 1,4-dioxane (20 mL) and water (4 mL) were added into a 25 mL round bottom flask one by one, the mixture was purged with argon for 3 times, and placed in an 110° C. oil bath for reaction overnight. After the reaction, the reaction solution was cooled, poured into water (10 mL), and then extracted with ethyl acetate (50 mL×3). The organic phases were combined and washed with saturated brine (20 mL×3), then dried over anhydrous sodium sulfate, filtered and concentrated. The residue was purified by column chromatography (dichloromethane/methanol=10/1) to obtain 4-(3-((3-(2-fluorophenyl)-5-methyl-5,6-dihydropyrrolo[3,4-c]pyrazole-2(4H)-yl)methyl)phenyl)-3-tert-butyl ester, -1,6-dihydropyridine-1(2H)-carboxylic acid tert-butyl ester 9d (200 mg, brown oil), yield: 23%. MS m/z (ESI): 489.4 [M+H].

The Fourth Step 3-(2-fluorophenyl)-5-methyl-2-(3-(1,2,3,6-tetrahydropyridin-4-yl)benzyl)-2,4,5,6-tetrahydropyrrolo[3,4-C]pyrazole (3-chlorobenzyl)-3-(2-fluorophenyl)-5-methyl-2,4,5,6-tetrahydropyrrolo[3,4-c]pyrazole 3e (600 mg, 1.76 mmol), 4-(4,4,5,5-tetramethyl-1,3,2-dioxaborolan-2-yl)-3,6-dihydropyridine-1(2H)-Tert-butyl carboxylate 9c (1.1 g, 3.52 mmol), sodium bicarbonate (739 mg, 8.80 mmol), tris (dibenzylideneacetone)dipalladium (161 mg, 0.176 mmol), 2-dicyclohexylphosphine-2',4',6'-triisopropylbiphenyl (168 mg, 0.352 mmol), 1,4-dioxane (20 mL) and water (4 mL) were added into a 25 mL round bottom flask one by one, and the mixture was stirred overnight at room temperature. The reaction solution was concentrated, and the residue was prepared by HPLC (acetonitrile/water (containing 0.05% trifluoroacetic acid) gradient washing) to obtain the target compound 3-(2-fluorophenyl)-5-methyl-2-(3-(1),2,3,6-Tetrahydropyridin-4-yl)benzyl)-2,4,5,6-tetrahydropyrrolo[3,4-C]pyrazole 9 (trifluoroacetate, salt coefficient=2.7, salt-containing molecular weight: 696.33, 7.80 mg, yellow oil). MS m/z (ESI): 389.5 [M+H]. $^1$H NMR (400 MHz, MeOD) δ 7.58-7.50 (m, 1H), 7.43-7.37 (m, 1H), 7.36-7.21 (m, 4H), 7.10 (s, 1H), 6.93 (d, J=8.0 Hz, 1H), 6.04 (s, 1H), 5.37 (s, 2H), 4.59 (m, 4H), 3.82 (s, 2H), 3.43 (t, J=4.0 Hz, 2H), 3.18 (s, 3H)), 2.73-2.65 (m, 2H).

Example 10

2-(3-(3,6-dihydro-2H-pyran-4-yl)benzyl)-3-(2-fluoropyridin-3-yl)-5-methyl-2,4,5,6-tetrahydropyrrolo[3,4-c]pyrazole

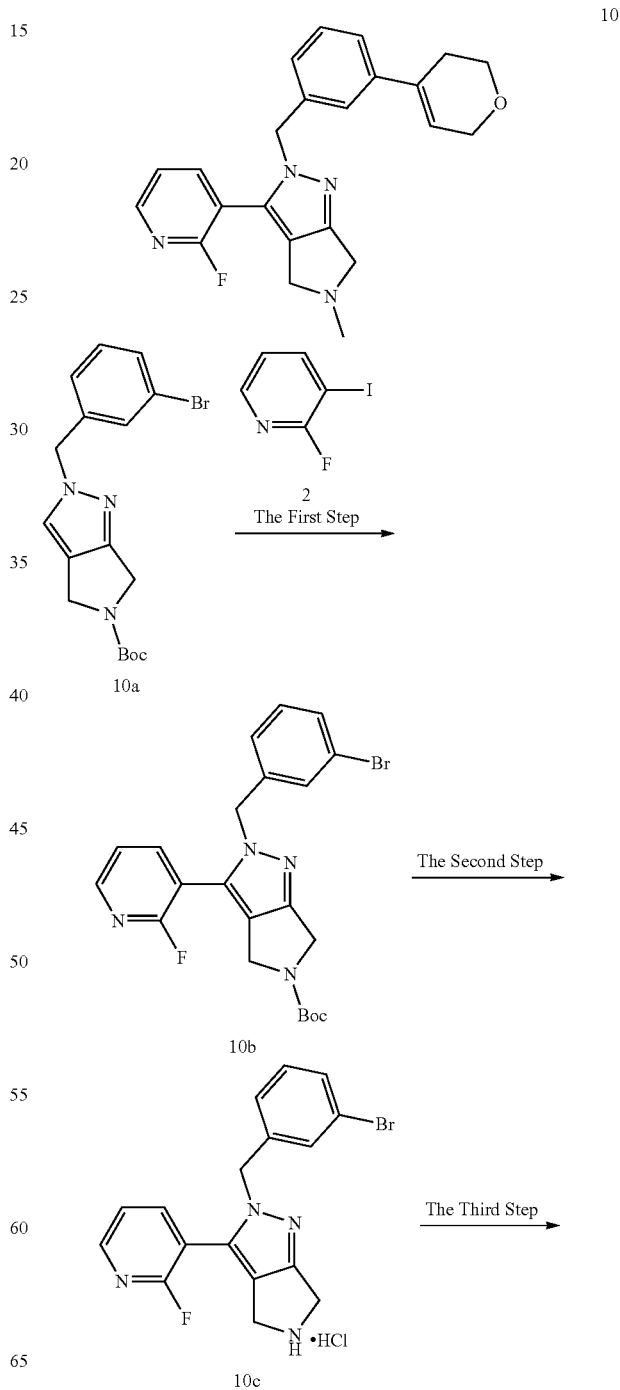

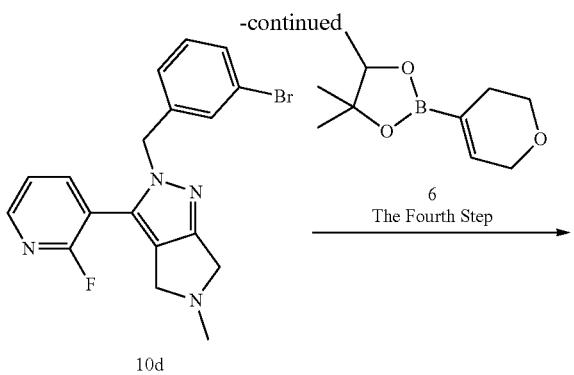

The First Step

2-(3-bromobenzyl)-3-(2-fluoropyridin-3-yl)-2,6-dihydropyrrolo[3,4-c]pyrazole-5(4H)-carboxy tert-butyl ester 2-(3-bromobenzyl)-2,6-dihydropyrrolo[3,4-c]pyrazole-5 (4H)-carboxylic acid tert-butyl ester 10a (11.4 g, 30 mmol), potassium acetate (17.6 g, 180 mmol), allyl palladium(II) chloride dimer (1.1 g, 3 mmol), N,N-dimethylacetamide (100 mL) and 2-fluoro-3-Iodopyridine (13.4 g, 60 mmol) were added into a round bottom flask one by one. After the oil pump was purged (nitrogen) for four times, the mixture was placed in an oil bath that was heated to 150° C. in advance for reaction for 5 hours. After the reaction was returned to room temperature, the reaction solution was poured directly into water (80 mL), and extracted with ethyl acetate (150 mL×3). The organic phase was washed with brine (40 mL×2), then dried over anhydrous sodium sulfate, filtered and concentrated. The crude product was separated by combi-flash (normal phase silica gel column, 80 g, petroleum ether:ethyl acetate=0-30%) to obtain 2-(3-bromobenzyl)-3-(2-fluoropyridin-3-yl)-2,6-Dihydropyrrolo[3, 4-c]pyrazole-5(4H)-carboxylic acid tert-butyl ester 10b (2.36 g, yellow oil), yield: 16.6%. MS m/z (ESI): 473/475 [M+H]. $^1$H NMR (400 MHz, CD3OD) δ 8.28 (d, J=4.0 Hz, 1H), 7.90 (t, J=8.0 Hz, 1H), 7.43-7.33 (m, 2H), 7.21-7.11 (m, 2H), 6.93 (d, J=8.0 Hz, 1H), 5.32 (s, 2H), 4.53 (s, 1H), 4.51 (s, 1H), 4.43 (s, 1H), 4.41 (s, 1H), 1.51 (s, 9H).

The Second Step

2-(3-bromobenzyl)-3-(2-fluoropyridin-3-yl)-2,4,5,6-tetrahydropyrrolo[3,4-c]pyrazole hydrochloride The hydrochloric acid/methanol solution (3M, 3.3 mL) was added into 2-(3-bromobenzyl)-3-(2-fluoropyridin-3-yl)-2,6-dihydropyrrolo[3,4-c]Pyrazole-5(4H)-tert-butyl carboxylate 10b (2.36 g, 2.5 mmol) in methanol (8.0 mL) for reaction at room temperature for 1 hour. After the reaction, the crude product 2-(3-bromobenzyl)-3-(2-fluoropyridin-3-yl)-2,4,5,6-tetrahydropyrrolo[3,4-c]pyrazole hydrochloride 10c (3.8 g, brown oil) was obtained by direct concentration, yield: 94%. MS m/z (ESI): 375.0 [M+H].

The Third Step

2-(3-bromobenzyl)-3-(2-fluoropyridin-3-yl)-5-methyl-2,4,5,6-tetrahydropyrrolo[3,4-c]pyrazole Aqueous formaldehyde solution (37%, 2.07 g, 24 mmol) was added into 2-(3-bromobenzyl)-3-(2-fluoropyridin-3-yl)-2,4,5,6-tetrahydropyrrolo[3,4-c]pyrazole hydrochloride 10c ((581 mg, 1.45 mmol) in methanol (10 mL) solution, and stirred at room temperature for half an hour. Glacial acetic acid (2 mL) and sodium acetate borohydride (3.4 g, 16 mmol) were slowly added into the reaction solution for reaction at room temperature overnight. The reaction solution was concentrated, dissolved and diluted with dichloromethane (90 mL), and then washed with ammonia/water (10 mL×2, ⅕), saturated brine (20 mL), and the organic phase was dried and concentrated with anhydrous sodium sulfate. The residue was separated with combi-flash (normal phase silica gel column, 20 g, dichloromethane: dichloromethane/methanol mixed solvent (volume ratio v/v=10/1)= 0-50%) to obtain 2-(3-bromobenzyl)-3-(2-fluoropyridin-3-yl)-5-methyl-2,4,5,6-tetrahydropyrrolo[3,4-c] pyrazole 10d (1.0 g, yellow oil), yield: 66.7%. MS m/z (ESI): 387.0 [M+H].

The Fourth Step

2-(3-(3,6-dihydro-2H-pyran-4-yl)benzyl)-3-(2-fluoropyridin-3-yl)-5-methyl-2,4,5,6-tetrahydropyrrolo[3,4-c]pyrazole 2-(3-Bromobenzyl)-3-(2-fluoropyridin-3-yl)-5-methyl-2, 4,5,6-tetrahydropyrrolo[3,4-c]pyrazole 10d (80 mg, 0.21 mmol), 3,6-dihydropyran-4-borate (53 mg, 0.25 mmol), [1,1'-bis(diphenylphosphino)ferrocene]palladium dichloride (15 mg, 0.02 mmol), potassium carbonate (58 mg, 0.42 mmol), dioxane (0.8 mL) and water (0.2 mL) were sequentially added into a microwave tube. After purging (argon) for three times, the oil bath was heated to 80° C., and the temperature was kept and stirred for 1.5 hours. After the reaction, the mixture was cooled to room temperature, filtered, and the filtrate was extracted with ethyl acetate (30 mL×3). The organic phase was washed with brine (10 mL×2), then dried over anhydrous sodium sulfate, filtered and concentrated. The crude product was separated by combi-flash (normal phase silica gel column, 25 g, dichloromethane: dichloromethane/methanol mixed solvent (volume ratio v/v=10/1)=0-50%) to obtain the crude product, and then prepared by HPLC (Acetonitrile/water (containing 0.05% trifluoroacetic acid) gradient washing), purification to obtain the target compound 2-(3-(3,6-dihydro-2H-pyran-4-yl) benzyl)-3-(2-fluoropyridin-3-yl)-5-methyl-2,4,5,6-tetrahydropyrrolo[3,4-c]pyrazole 10 (trifluoroacetate, salt coefficient=3.06, salt-containing molecular weight: 739.35, 9.76 mg, colorless solid), yield: 11.9%. MS m/z (ESI): 391.4 [M+H]. $^1$H NMR (400 MHz, CD3OD) δ 8.30 (d, J=4.0 Hz, 1H), 7.84 (t, J=8.0 Hz, 1H), 7.42 (t, J=6.0 Hz, 1H), 7.30 (d, J=8.0 Hz, 1H), 7.21 (t, J=6.0 Hz, 1H), 7.02 (s, 1H), 6.88 (d, J=8.0 Hz, 1H), 6.06 (s, 1H), 5.40 (s, 2H), 4.74-4.40 (m, 4H), 4.27-4.24 (m, 2H), 3.88 (t, J=6.0 Hz, 2H), 3.18 (s, 3H), 2.42-2.36 (m, 2H).

Test Example: Determination of Compounds' Inhibition of H+/K+ ATPase Enzyme Activity The following experiment is used to determine the inhibitory effect of the compound of the present invention on the H+/K+ ATPase enzyme activity.

1. Experimental Materials
   Plate reader: SpectraMax M5(MD)
   Malachite Green (Sigma Aldrich, 213020-25G)
   Ammonium molybdate (Sigma Aldrich, 277908-20G)
   ATP (Sigma Aldrich, A1852-1VL).
2. Buffer Preparation
   Enzyme working solution: titrating the enzyme, diluting the enzyme with buffer solution 1, and taking 5 μl of the diluted solution into 50 μl reaction system
   ATP solution: 100 mM ATP was diluted to 5 mM with no K+ buffer, and 5 μl of the diluted solution was added to the 50 μl reaction system, that is, the final concentration of ATP was 500 μM MLG color development liquid: 0.12% MLG, 7.5% ammonium molybdate, 11% Tween-20 was mixed as 100:25:2, and adding 15 μl of the mixture into each well during detection.
   Buffer 1: 50 mM Tris-HCl pH 6.5, 5 mM magnesium chloride (magnesium chloride), 10 μM valinomycin (valinomycin)
   Buffer 2: 50 mM Tris-HCl pH 6.5, 5 mM magnesium chloride (magnesium chloride), 10 μM valinomycin (valinomycin), 20 mM KCl
   Homogenization buffer: 10 mmol/L Tris-HCl, pH 6.8, 0.25 M sucrose (sucrose), 1 mmol/LEDTA 7.5% Ficoll layering solution: homogenization buffer+7.5% (W/W) (Ficoll 400).
3. Experimental Steps
3.1. W/K+ ATPase Enzyme Extraction
   (1) The stomach tissue of the rabbit was separated, and the blood was washed with tap water, food residue.
   (2) The fundus portion was thoroughly washed with pre-cooled NaCl solution to remove surface mucus.
   (3) The stripped mucosa was filled into a sample bag or a 50 ml centrifuge tube, and quickly freezing in a liquid nitrogen tank.
   (4) The tissue was removed, minced with surgical scissors, and a pre-cooled homogenization buffer (4 ml/g tissue) was added and homogenized in a tissue homogenizer for 2 to 10 minutes.
   (5) After homogenization, if there were larger tissue particles, they could be removed by centrifugation (600 g, 10 min), and then the supernatant was transferred to a clean centrifuge tube. After centrifugation at 20000 g for 30 minutes, then the supernatant was transferred to a clean centrifuge tube at 100000 g for 90 minutes, and the precipitate was collected.
   (6) Resuspending the precipitate with homogenization buffer, blowing uniformly, adding 7.5% Ficoll layering solution at equal ratio, centrifuging at 100000 g for 90 minutes, and collecting the precipitate.
   (7) Resuspending the precipitate with homogenization buffer, blowing uniformly, and the protein concentration was measured by Bradford. Freezing in tubes at −80° C. for later use.
3.2. H+/K+ ATPase Activity Experiment
   (1) Adding 35 μl of reaction buffer to each experimental well, and then adding 35 μl of buffer 1.
   (2) Adding 5 μl buffer 1 containing 10% DMSO to the whole enzyme and buffer well.
   (3) Adding 5 μl of 10× compound working solution to the compound well and mixing well.
   (4) Adding 5 μl of buffer 1 to the buffer well.
   (5) Adding 5 μl of 10× enzyme working solution to the remaining wells, mixing and incubating at 37° C. for 30 minutes.
   (6) Adding 5 μl of 10×ATP working solution to all experimental wells, mixing and incubating at 37° C. for 20 min.
   (7) Adding 15 μl MLG chromogenic solution to all experimental wells, and uniformly mixing and incubating at room temperature for 5-30 min.
   (8) The reading number of 620 nm was detected by an M5 instrument.
4. Data Analysis
   The inhibition rate is calculated with the following formula:

Inhibition rate ($IC_{50}$)=[OD (sample well)−OD (full enzyme well containing potassium chloride)]/[(OD (full enzyme well containing potassium chloride)−OD (full enzyme well without potassium chloride)]×100%

5. Experimental Results
   The inhibition rate ($IC_{50}$) of each example compound is shown in Table 2.

TABLE 2

| Compound number | $IC_{50}(\mu M)$ |
|---|---|
| Example 1 | 0.2334 |
| Example 2 | 0.05593 |
| Example 3 | 0.1966 |
| Example 4 | 0.1133 |
| Example 5 | 0.08827 |
| Example 6 | 0.1212 |
| Example 7 | 0.1144 |
| Example 8 | 0.08111 |
| Example 9 | 0.2075 |
| Example 10 | 0.7688 |

As can be seen from Table 2, the compounds of the present invention have excellent H+/K+ ATPase enzyme inhibitory activity.

The invention claimed is:
1. A compound represented by formula (I):

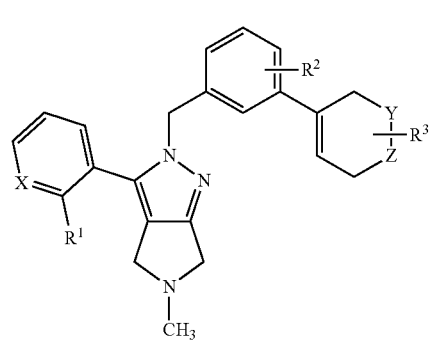

or a pharmaceutically acceptable salt, stereoisomer, or tautomer thereof, wherein:
  X is CH or N;
  R¹ is halogen;
  R² is H, halogen, or OH;
  R³ is H or C$_{1-3}$ alkyl;
  Y is —CH$_2$—, —NH—, or —O—; and
  Z is —CH$_2$—, —NH—, or —O—;
  with the proviso that Y and Z are not both —CH$_2$—.

2. The compound of claim 1, or a pharmaceutically acceptable salt, stereoisomer, or tautomer thereof,
wherein:
  R¹ is F;
  R² is H, F, Cl, or OH;
  R³ is H; and
  (i) Y is —O—; and
    Z is —CH$_2$—; or
  (ii) Y is —CH$_2$—; and
    Z is —NH— or —O—.

3. The compound of claim 2, wherein the compound is selected from the group consisting of:

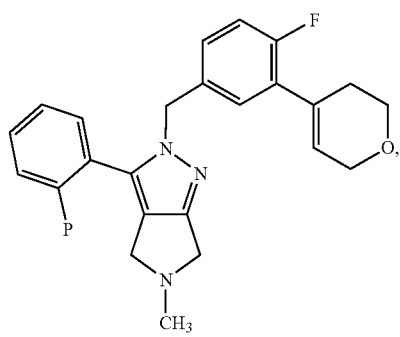
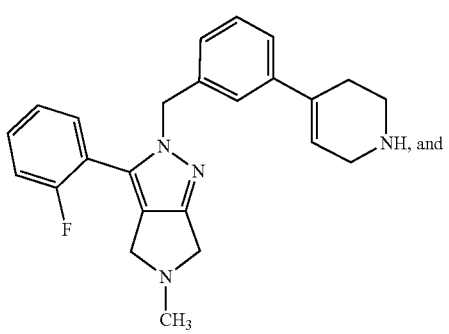
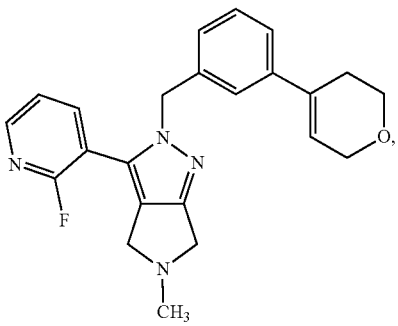
or a pharmaceutically acceptable salt or tautomer thereof.
4. A pharmaceutical composition comprising a pharmaceutically acceptable carrier, excipient, or diluent and the compound of claim 1, or a pharmaceutically acceptable salt, stereoisomer, or tautomer thereof.
* * * * *